(12) United States Patent
Verenchikov

(10) Patent No.: US 9,984,863 B2
(45) Date of Patent: May 29, 2018

(54) MULTI-REFLECTING TIME-OF-FLIGHT MASS SPECTROMETER WITH AXIAL PULSED CONVERTER

(71) Applicant: LECO Corporation, St. Joseph, MI (US)

(72) Inventor: Anatoly N. Verenchikov, St. Petersburg (RU)

(73) Assignee: LECO Corporation, St. Joseph, MI (US)

( * ) Notice: Subject to any disclaimer, the term of this patent is extended or adjusted under 35 U.S.C. 154(b) by 0 days. days.

(21) Appl. No.: 15/300,998

(22) PCT Filed: Mar. 31, 2015

(86) PCT No.: PCT/US2015/023621
§ 371 (c)(1),
(2) Date: Sep. 30, 2016

(87) PCT Pub. No.: WO2015/153630
PCT Pub. Date: Oct. 8, 2015

(65) Prior Publication Data
US 2017/0032952 A1 Feb. 2, 2017

Related U.S. Application Data

(60) Provisional application No. 61/973,117, filed on Mar. 31, 2014.

(51) Int. Cl.
*H01J 49/40* (2006.01)
*G01N 30/72* (2006.01)
(Continued)

(52) U.S. Cl.
CPC ............ *H01J 49/403* (2013.01); *G01N 30/72* (2013.01); *H01J 49/0031* (2013.01); *H01J 49/406* (2013.01); *H01J 49/44* (2013.01)

(58) Field of Classification Search
CPC ........ H01J 49/40; H01J 49/025; G01T 1/2006
See application file for complete search history.

(56) References Cited

U.S. PATENT DOCUMENTS 5,614,711 A 3/1997 Li et al.
5,625,184 A 4/1997 Vestal et al.
(Continued)

FOREIGN PATENT DOCUMENTS

GB 2403063 A 12/2004
GB 2478300 A 9/2011
(Continued)

OTHER PUBLICATIONS

International Search Report dated Jun. 30, 2015, relating to International Application No. PCT/US2015/023621.
(Continued)

*Primary Examiner* — Eliza Osenbaugh-Stewart
(74) *Attorney, Agent, or Firm* — Honigman Miller Schwartz and Cohn LLP

(57) ABSTRACT

Apparatuses and methods for time-of-flight mass spectrometry providing effective pulsed conversion of continuous ion beams into pulsed ion packets is disclosed. Bunching of energetic continuous ion beams forms ion packets, which are filtered by a subsequent isochronous energy filter. The bunching method is particularly suitable for ion sources with relatively large spatial emittance, otherwise unable to fir the acceptance of orthogonal accelerators. The method is particularly suitable for multi-reflecting TOF MS, which accommodates small size ion packets and where the duty cycle advantage of orthogonal accelerators is minor.

50 Claims, 14 Drawing Sheets

(51) Int. Cl.
*H01J 49/00* (2006.01)
*H01J 49/44* (2006.01)

(56) References Cited

U.S. PATENT DOCUMENTS

| | | |
|---|---|---|
| 5,689,111 A | 11/1997 | Dresch et al. |
| 5,739,529 A | 4/1998 | Laukien et al. |
| 5,760,393 A | 6/1998 | Vestal et al. |
| 6,300,627 B1 | 10/2001 | Koster et al. |
| 6,348,688 B1 | 2/2002 | Vestal |
| 6,512,225 B2 | 1/2003 | Vestal et al. |
| 6,541,765 B1 | 4/2003 | Vestal |
| 6,621,074 B1 | 9/2003 | Vestal |
| 6,703,608 B2 * | 3/2004 | Holle .................... H01J 49/40 250/282 |
| 6,717,131 B2 | 4/2004 | Holle et al. |
| 6,770,870 B2 | 8/2004 | Vestal |
| 7,045,792 B2 | 5/2006 | Parr et al. |
| 7,667,195 B2 | 2/2010 | Vestal |
| 8,461,521 B2 | 6/2013 | Vestal |
| 2006/0214100 A1* | 9/2006 | Verentchikov ........ H01J 49/406 250/287 |
| 2007/0029473 A1 | 2/2007 | Verentchikov |
| 2007/0176090 A1 | 8/2007 | Verentchikov |
| 2008/0185511 A1 | 8/2008 | Senko |
| 2010/0181473 A1* | 7/2010 | Blenkinsopp .......... H01J 49/40 250/282 |
| 2012/0016861 A1 | 1/2012 | Edwards et al. |
| 2012/0091332 A1 | 4/2012 | Makarov et al. |
| 2013/0048852 A1* | 2/2013 | Verenchikov ....... H01J 49/0031 250/282 |
| 2013/0068942 A1 | 3/2013 | Verenchikov |

FOREIGN PATENT DOCUMENTS

| | | |
|---|---|---|
| SU | 1681340 A1 | 9/1991 |
| WO | WO-2005001878 A2 | 1/2005 |
| WO | WO-2006102430 A2 | 9/2006 |
| WO | WO-2007044696 A1 | 4/2007 |
| WO | WO-2011-107836 A1 | 9/2011 |
| WO | WO-20110135477 A1 | 11/2011 |
| WO | WO-2012/024468 A2 | 2/2012 |
| WO | WO-2013/063587 A2 | 5/2013 |
| WO | WO-2013067366 A2 | 5/2013 |
| WO | WO-2013134165 A1 | 9/2013 |
| WO | WO-2013192161 A2 | 12/2013 |
| WO | WO-2014176316 A2 | 10/2014 |

OTHER PUBLICATIONS

Wolfgang R. Plab, et al., "Multiple-reflection time-of-flight mass spectrometry", International Journal of Mass Spectrometry, vol. 349-350 (2013), pp. 134-144.

* cited by examiner

Fig. 7A
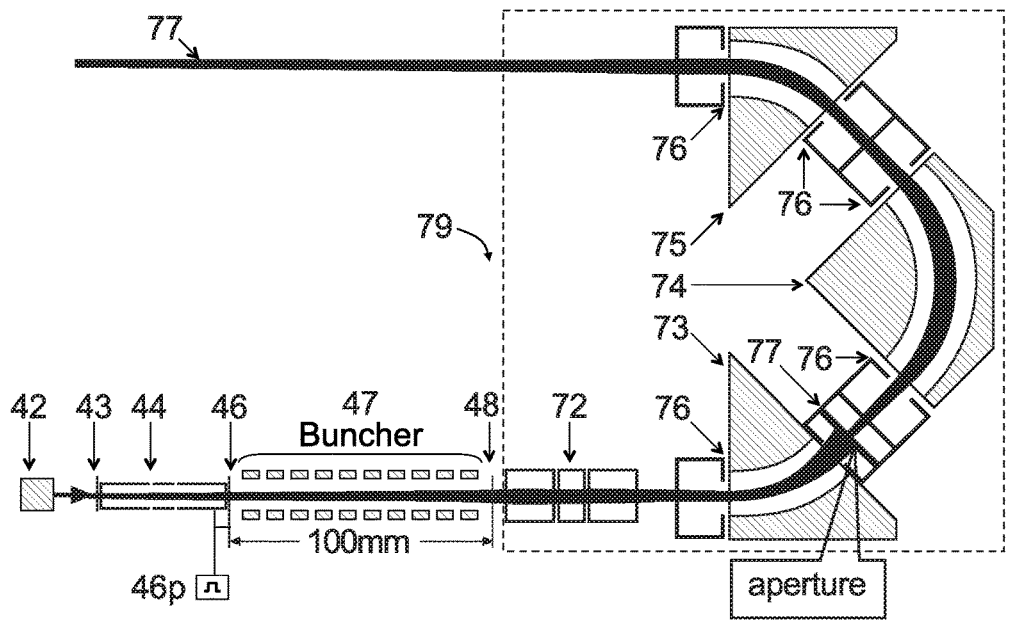
Fig. 7B
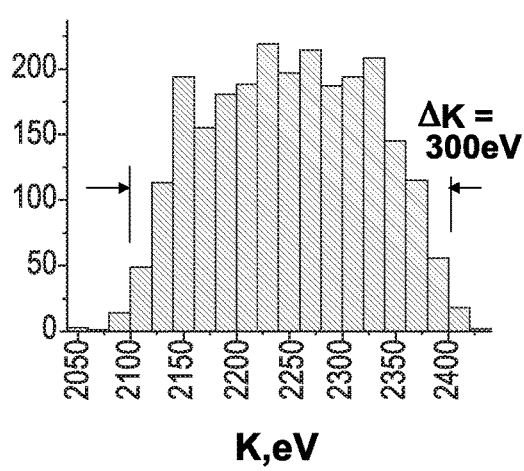
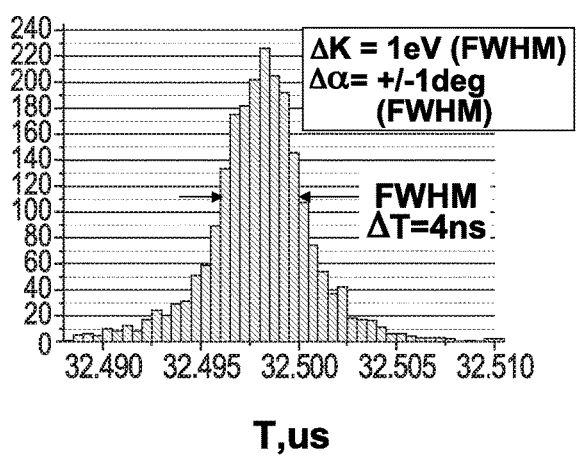

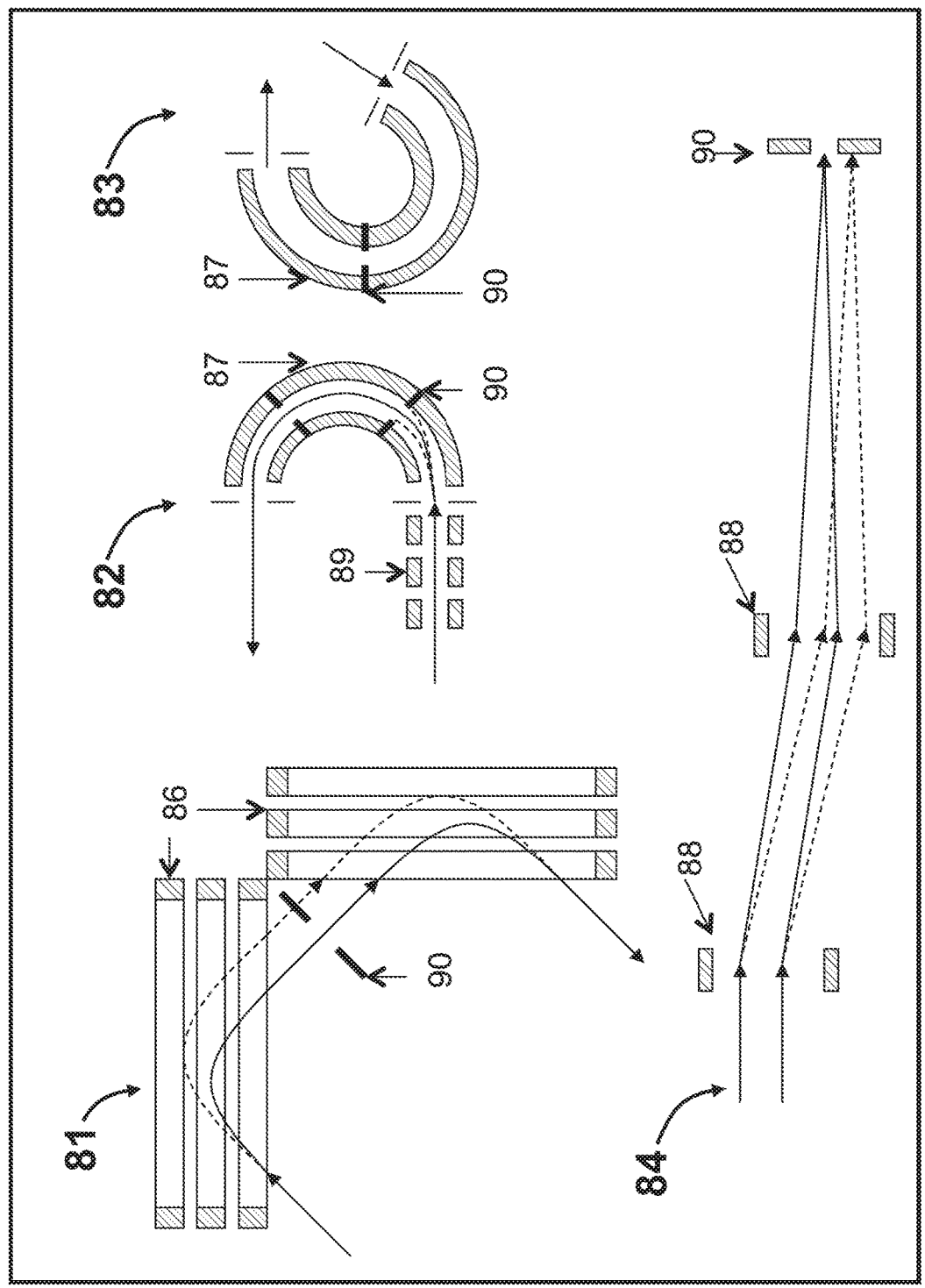

MULTI-REFLECTING TIME-OF-FLIGHT MASS SPECTROMETER WITH AXIAL PULSED CONVERTER

CROSS-REFERENCE TO RELATED APPLICATIONS

This application claims priority under 35 U.S.C. § 371 to Patent Cooperation Treaty Application No. PCT/US2015/023621, filed Mar. 31, 2015, which claims priority under 35 U.S.C. § 119(e) to U.S. Provisional Application No. 61/973,117, filed Mar. 31, 2014. The disclosures of these prior applications are considered part of the disclosure of this application and are hereby incorporated by reference in their entireties.

TECHNICAL FIELD

This disclosure relates to time-of-flight mass spectroscopic analysis and to an improved method of pulsed ion conversion for singly reflecting and multi-reflecting time-of-flight mass spectrometers.

BACKGROUND

Time-of-flight mass spectrometers (TOF MS) determine the mass-to-charge ration (m/z) of an ion by accelerating ions through the TOF MS towards a detector and recording a measurement for the ion travel time within the TOF MS to the detector. Some implementations have utilized two TOF MS consecutively (TOF/TOF). Other implementations of TOF MS may include gas chromatography (GC-TOF MS) or liquid chromatography (LC-TOF MS) to handle a sample before TOF MS carry out the analysis. Additionally, such implementations of GC-TOF MS and LC-TOF MS may utilize a quadrupole ion trap (LC-Q-TOF and GC-Q-TOF), such as U.S. Patent Application 2013/0068942 incorporated herein by reference.

Parameters of TOF MS depend on efficient coupling to pulsed and continuous ion sources. To form ion packets, TOF MS commonly employ pulsed acceleration of stagnated ion clouds. In early implementations, ions were accumulated in electron impact (EI) ion sources and were pulse-accelerated into a TOF MS. A method of delayed ion extraction from an EI source was proposed in [W. C. Willey, I. H. McLaren, Rev. Sci. Instr. 26, 1150 (1955)] to improve the resolution of linear TOF MS. Dodonov et al., in SU 1681340, describe an effective solution for converting continuous ion beams into pulsed ion packets with the aid of an orthogonal accelerator (OA). In a sense, an ion beam is stagnated in the direction of TOF separation. Compared to the prior pulse deflection methods, the OA method strongly improves the duty cycle of pulsed conversion. The OA pulsed conversion method appears generic (i.e. applicable to any type of ion source) and has been widely adopted in commercial instrumentation for LC-TOF, LC-Q-TOF and GC-Q-TOF instruments.

Another method of preparing short ion packets—pulsed bunching of moving and initially wide ion packets—has been long-known in nuclear physics for transformations of ion packets in time-energy space. Such transformations of the ion packets include time compression, energy-spread reduction, or time-focal plane adjustment. To form initial ion packets (prior to the bunching step) nuclear physics commonly employs the chopping of continuous ion beams, say with mechanical choppers, like rotating disk with slits. Thus, while pulsed acceleration is applied to stagnated ion clouds, bunching is applied to already moving ion packets.

Axial pulsed bunching of ion packets has been adopted in the field of mass spectrometry and has been explored in matrix-assisted laser desorption ionization (MALDI) instrumentation. Delayed extraction (DE) in MALDI TOF employs bunching of short ion packets formed by a pulsed laser shot. As described in U.S. Pat. No. 5,760,393, U.S. Pat. No. 5,625,184, and U.S. Pat. No. 6,541,765 (each of which is incorporated herein by reference), this DE method has improved time-focusing and source robustness by avoiding energetic collisions between extracted ions and ejected material known as the MALDI plume. Applying axial bunching of ion packets in TOF-TOF tandems is described in U.S. Pat. No. 5,739,529, U.S. Pat. No. 6,703,608, U.S. Pat. No. 6,717,131, U.S. Pat. No. 6,300,627, U.S. Pat. No. 6,512,225, U.S. Pat. No. 6,621,074, U.S. Pat. No. 6,348,688, U.S. Pat. No. 6,770,870, U.S. Pat. No. 7,667,195, U.S. Pat. No. 8,461,521, WO2011028435, US2012168618, and WO2013134165, each of which is incorporated herein by reference. Bunching of moving ion packets was also proposed after pulse ejecting multipoles, as described in U.S. Pat. No. 5,689,111 (FIG. 8), which is incorporated herein by reference.

Known methods of pulsed conversion were initially adopted in recently emerged multi-reflecting Time-of-flight mass spectrometry (MR-TOF MS). MR-TOF MS with ion spatial confinement achieved by a periodic lens, described in GB2403063A and WO2005001878 (each of which are incorporated herein by reference), provides an exceptional combination of mass resolving power and data acquisition speed. Resolution is strongly enhanced, rising nearly proportional to flight path extension. While the flight path in singly reflecting TOF MS is about three times the instrument size, commercial MR-TOF MS Citius HRT by LECO Corp provides a 16 m flight path in a 0.6 m long analyzer (i.e. allows for trajectory folding at more than a factor of twenty-five). Potentially, the flight path can increased to few hundred meters in 1 m long instrument if using cylindrical analyzer geometry as described in GB2478300 and WO2011107836, which are incorporated herein by reference.

However, sensitivity of MR-TOF MS has been limited by the duty-cycle limitations of a pulsed converter. If employing an orthogonal accelerator (OA), as described in WO2007044696, the duty cycle is reduced to less than 0.3-0.5%—at a pulsing period of 1 ms and at an OA length of 6-8 mm—due to analyzer acceptance limitations. If employing and alternative axial trap converter, the charge throughput becomes limited to 1E+7-1E+8 ion/sec as described in "Linear Ion Trap with Axial Ejection as a Source for a TOF MS" by B. Kozlov et. al. ASMS 2005. With recent improvements of ion sources, like ESI sources providing 1E+9 ion/sec or EI sources providing up to 1E+11 ion/sec, the effective duty cycle of trap converters becomes even lower than the duty cycle of the OA.

The problem has been notably softened with introduction of the multiplexing method based on encoded frequent pulsing (EFP®), as described in WO2011135477, incorporated herein by reference. The average pulse frequency is increased from 1 kHz to 100 kHz, which improves the OA duty cycle to approximately 30% and which also improves both the dynamic range of the analyzer (limited to approximately 1000 ion/packet of one mass by space charge effects) and the dynamic range of the detector and data system. The method has been extended onto various tandems as described in WO2013067366, WO2013192161, and WO2014176316, each incorporated herein by reference.

The scheme of orthogonal acceleration (OA) has drawbacks. First, the OA scheme is very sensitive to minor distortions of field-free conditions when a slow continuous ion beam fills the OA gap. Surface and mesh contamination affect an ideal OA operation. Second, to form sharp ion packets, the beam spatial-angular emittance has to be low, usually under 100 eV*mm$^2$*deg$^2$, (which may be realized by 1-2 mm and 1-2 deg at 30-50 eV energy) which requires trimming of a continuous ion beam prior to OA and, thus, introduces ion losses. Collisional radiofrequency (RF) ion guides, like gas filled RF-only quadrupoles, help in significant reduction of ion beam emittance to keep those losses moderate. However, RF ion guides have limited charge throughput, and spatial losses at the OA entrance appear dependent on ion currents above 10 nA, when using intense sources such as EI or ICP. Third, reaching small turn-around times for higher resolving power requires large field strength in the OA and large amplitudes (above 2 kV) of pulse generators. This may require the use of at least two pulse generators, which adds cost and becomes challenging in combination with a 100 kHz pulsing rate when using encoded frequent pulsing. Fourth, further reduction of turn around time (desired for higher resolution) by using high acceleration fields in OA is limited by the associated rise of ion packet energy spread, exceeding MR-TOF energy acceptance.

Thus, there still remain some practical problems associated with orthogonal acceleration for MR-TOF MS. And a need remains for a lower cost and more effective solution for coupling continuous or quasi-continuous ion sources to MR-TOF analyzers.

SUMMARY

Pulsed conversion of continuous ion beams into pulsed packets becomes effective when applying axial bunching to the continuous ion beams followed by an energy filtering of ion packets to remove ions with excessive energy spread that do not fit the energy acceptance of a time-of-flight mass spectrometer. Preferably, a continuous ion beam is accelerated to medium energies (few hundred eV to a few keV) and is shaped for lower angular spread prior to the bunching step. Preferably, energy filtering is made with either curved electrostatic sectors or with angled gridless ion mirrors.

In multiple practical cases, the novel method of axial bunching is effective than the widely used orthogonal acceleration method. In spite of a slightly lower time duty cycle, the axial bunching method may result in higher efficiency, since it accepts much wider (by two orders of magnitude) emittance of the continuous ion beams and eliminates spatial losses in front of the OA. Axial bunching is capable of forming even shorter ion packets, though the method may also reduce the duty cycle. Axial bunching may use much smaller amplitudes of pulse generators, increasing convenience of the encoded frequent pulsing when utilizing high frequency pulsing.

Further analysis of the novel method reveals several fine advantages of the axial bunching scheme. The method allows fine control over spatial divergence, time, and energy spreads of ion packets to achieve high resolution, excellent peak shape, and high isobaric abundances in TOF MS. For most practical ion sources, the ion beam emittance appears sufficiently small to fit spatial acceptance of MR-TOF analyzers without adding time per spatial spread aberrations. Continuous acceleration of ion beams drops an absolute velocity spread and, thus, turnaround time may be notably reduced to the ins range. The energy filtering step also contributes by enabling the use of higher pulse amplitudes without affecting peak width by the excessive ion energy spread in the analyzer. Both of these means improve resolution and peak shape in TOF MS, though at the expense of the time duty cycle. But the duty cycle may be improved by the method of encoded frequent pulsing, and by using MR-TOF analyzers with yet wider energy acceptance (10-14%) as described in WO2013063587, which is incorporated herein by reference.

The inventors further realized that: (a) the axial bunching may be accomplished using a single pulse generator with limited pulse amplitudes; (b) axial bunching is more compatible with surface imaging in SIMS or MALD methods when applying methods of non-redundant sampling as described in WO2013192161, incorporated herein by reference; (c) the novel method can be employed at both stages of tandem mass spectrometers (i.e. at parent ion selection in TOF1 and at fragment ion analysis in TOF2) while using various fragmentation cells, either short CID at low gas pressure, a gas filled RF ion guide, a short SID cell with gliding collisions, or a planar SID oriented across an ion beam; (d) a higher duty cycle can be obtained when using a pulsed or a quasi-continuous ion source—though at the expense of analyzed mass range—applied at target GC-MS analysis or when selecting parent ions; (e) the duty cycle increases when using a wide bore and high multipole RF-only ion guide to form a wide continuous ion beams that preferably includes smaller energy and angular spreads.

According to a first aspect of the disclosure, a time-of-flight mass spectrometer sequentially includes an ion source, an acceleration stage, a pulsed buncher, an isochronous energy filter, and a time-of-flight mass analyzer. The ion source may be a continuous or quasi-continuous ion source that generates an ion beam. The acceleration stage continuously accelerates the ion beam to an energy level that is at least ten times greater than an initial energy spread of the ion beam. The pulsed buncher has at least one electrode connected to a pulsed voltage supply for ion acceleration or deceleration substantially along the beam direction. The isochronous energy filter transmits ions within an energy acceptance range of a time-of-flight analyzer. The time-of-flight mass analyzer may be embodied as a singly reflecting TOF MS or a MR-TOF MS. Additionally, the time-of-flight mass analyzer has a time-of-flight detector.

Implementations of this aspect of the disclosure optionally include one or more of the following features. In some implementations, the apparatus further includes a suppressor that rejects ions approaching the buncher that have an energy level that is affected by the bunching pulse. The suppressor includes at least one electrode connected to a pulse generator. In other implementations, no suppressor is included but the energy filter is arranged to remove ions of unwanted "boundary" energies to eliminate decelerated ions formed at the accelerator boundaries. Optionally, the continuous or quasi-continuous ion source generates an ion beam with an energy spread less than 10 eV. And the apparatus optionally further includes a spatially focusing lens in front of the pulsed buncher for to: (i) reduce the ion beam angular spread, so that axial energy spread within the pulsed buncher remains comparable to an initial energy spread past said ion source; and/or (ii) spatially focus the ion packets onto a slit or an aperture of the energy filter. Additionally, the apparatus optionally may include a data acquisition system that triggering the pulsed buncher and records a waveform signal from the detector. In some implementations, the energy filter has an aperture or a slit at a plane of ion packet spatial/angular focusing for central ion energy and at least one chromatic ion optical element of the group of: (i) an isochronous electrostatic sector; (ii) a spatially focusing and isochronous grid less ion mirror; (iii) a pair of deflectors; (v) a set of periodic lens; (vi) at chromatic lens; (vii) a combination of the above elements. The pulsed buncher optionally includes a pulse generator with average frequency of at least 50 KHz, the data acquisition system optionally includes a triggering clock with capability of forming a preset string of pulses with mostly unique time intervals between pulses, and the data acquisition system optionally decodes partially overlapping spectra based on mostly unique pulse intervals.

In other embodiments, the apparatus includes a dual or single stage chromatograph prior to the ion source, which may include: (i) a closed electron impact ion source; (ii) a semi-open electron impact ion source with a total opening sized between 0.1 and 1 $cm^2$ and positively biased electron slits; (iii) a chemical ionization source; (iv) a chemical ionization source upstream of an electron impact ion source; (v) a photo-chemical ionization source; (iv) conditioned glow discharge ion source; (vi) a cold electron impact ion source with analyte internal energy cooling in supersonic gas jet; and (vii) a field ionization source. In other embodiments, the apparatus includes a gas filled RF only ion guide between the ion source and the continuous accelerator, and the ion source is optionally embodied as one of: (i) an ESI ion source; (ii) an APCI ion source; (iii) an APPI ion source; (iv) a gas filled MALDI ion source; (v) an EI ion source; (vi) a CI ion source; (vii) a cold EI ion source; (viii) a photo-chemical ionization ion source; and (ix) a conditioned glow discharge ion source. Optionally, the apparatus may further include one ion manipulation device between the ion source and the RF ion guide, and the ion manipulation device may be embodied as one of: (i) a quadrupole mass analyzer; (ii) a time-of-flight mass analyzer; (iii) a trap array mass analyzer; (iv) an ion mobility separator; and (v) a fragmentation cell. In other implementations, the ion source or the RF ion guide may have means for ion accumulation and pulsed ejection of ion packets at an energy spread under 10 eV.

The detector may include a conductive plate for converting impinging ion packets into secondary electrons. In this case, the converter plate is floated negative relative to a drift region of the spectrometer and is aligned parallel to a time front of the detected ion packets. Further in this case, the detector includes at least one magnet for steering the electrons at an angle between 30 and 180 degrees, a scintillator coated or covered by a conductive mesh (a potential of said mesh is adjusted at least 1 kV more positive than the converter plate), and a sealed photo-electron multiplier placed past said scintillator.

According to a second aspect of the disclosure, a method time-of-flight mass spectrometric analysis sequentially includes: (a) ionizing ions in an ion source and generating a continuous or quasi-continuous ion beam with initial energy spread under 10 eV; (b) continuously accelerating the ion beam to a mean energy at least 10 times larger than the initial energy spread; (c) spatially focusing the ion beam at a plane of spatial focusing while maintaining ion angular spread within a limit so that axial ion energy spread remains comparable to the initial energy spread; (d) bunching the continuous ion beam with a pulsed accelerating or decelerating electric field having one boundary in time and another in space of bunching region, thus forming ion packets; (e) isochronously filtering energy of the ion packets at chromatic deflecting or focusing of the ion packets and removing ions with unwanted energies on at least one aperture, located in the plane of spatial/angular focusing, while passing through ions that fit within the energy acceptance of the subsequent time-of-flight mass analysis step; (f) separating ion packets in time at isochronous single or multiple reflections in electrostatic field of at least one ion mirror; (g) detecting the ion packets with a time-of-flight detector to form waveform signal; and (h) analyzing the signal to extract mass spectral information.

Implementations of this aspect of the disclosure may include one or more of the following features. Preferably, the method further comprises a step of rejecting ions whose energies are affected by the bunching step to reside outside of the bunching boundaries. Alternatively, the step of energy filtering may be arranged to remove ions at unwanted, "boundary" energies to eliminate decelerated ions forming at the accelerator boundaries. Preferably, said step of isochronous energy filtering may include a step of ion packet skimming by an aperture or a slit and a step of isochronous and chromatic ion beam focusing or deflection by one electrostatic field of the group: (i) a deflecting field of an electrostatic sector; (ii) an angled reflecting field of a grid-less ion mirror; (iii) a deflecting field of at least one pair of deflectors; (v) a periodic spatial focusing field of a periodic lens; (vi) a focusing filed of at least one chromatic lens; and (vii) a combination of the above fields. Preferably, for the purpose of increasing the dynamic range of the method, the step of pulsed bunching may be arranged at periods at least 10 times smaller compared to ion flight time at the time separation step and the method may further comprise a step of encoding the bunching pulses with mostly unique time intervals between adjacent pulses at time increments no less than ion packet time width at the detection step and may also further comprise a step of decoding partially overlapped signals corresponding to multiple bunching pulses at the spectral analysis step.

Preferably, the method may further include a step of dual or single stage chromatographic separation prior to the ionization step; and wherein the ionization step may include one of the following: (i) ionizing by electron beam within a volume with an opening under 0.1 $cm^2$; (ii) ionizing by electron beam within a volume with total opening between 0.1 and 1.0 $cm^2$ and removing secondary electrons by positively biasing electrode in the vicinity of the ionizing electron beam; (iii) chemical ionization; (iv) chemical ionization of electron impact ionization for alternating ionization methods; (v) photo-chemical ionization; (iv) conditioned glow discharge ionization; (vi) cold EI ionization (i.e. electron impact ionization accompanied by the analyte internal molecular cooling in a supersonic gas jet); and (vii) field ionization. Preferably, the method may further include a step of ion beam confinement in gas collisions within radial non-uniform RF field of an RF ion guide between the ionization step and the continuous acceleration step; and wherein the ionization step may include one of the following: (i) ESI ionization; (ii) APCI ionization; (iii) APPI ionization; (iv) MALDI ionization at fore-vacuum gas pressure; (v) EI ionization; (vi) CI ionization; (vii) cold EI ionization; (viii) photo-chemical ionization; and (ix) conditioned glow discharge ionization. Preferably, the method may further include one ion manipulation step between the ionization step and the gaseous ion confinement step; and wherein the ion manipulation may include one of or a combination of the following: (i) mass separation in quadrupolar RF and DC fields; (ii) time-of-flight mass separation; (iii) trapping of ions in an array of RF and DC field traps followed by a sequential mass dependent ion ejection out of the array of trapping fields; (iv) an ion mobility separation; and (v) fragmenting ions. Preferably, the method may further include a step of ion accumulation and pulsed ejection of ion packets at the ionization step or the step of ion confinement in gaseous RF ion guide.

Preferably, for the purpose of improving dynamic range of the analysis, the ion packet detection step may include the following sequential steps: (i) aligning a conductive plate parallel to time front of said detected ion packets; (ii) arranging an accelerating field near the conductive plate surface; (iii) converting impinging ion packets into secondary electrons; (iv) steering said electrons by an angle between 30 and 180 degrees within magnetic field from 30 to 300 Gauss; (iv) accelerating the secondary electrons by at least 1 kV; (v) directing the secondary electrons onto a scintillator thus producing photons; (v) drawing electrostatic charge from a surface of the scintillator by surface electric leak or discharge towards a conductive mesh, which either covers or coats a surface of the scintillator; and (vi) detecting the photons by a sealed photo-electron multiplier, placed past the scintillator.

Preferably, for the purpose of adding MS-MS capabilities, after the time separation step in electrostatic fields of a time-of-flight analyzer, the method may further include a step of timed ion selection and a step of ion fragmentation of the group: (i) a surface induced dissociation SID on a surface arranged parallel to time-front and facing primary ion packets; (ii) a surface induced dissociation SID arranged at gliding angle relative to trajectory of parent ion packets; (iii) a collisional induced dissociation CTD within a short CID cell with length L under one centimeter at a gas pressure P adjusted to maintain a product P*L between 1 and 5 cm*mTor, which corresponds to single average collision of parent ions; (iv) a collisional induced dissociation CID arranged within said source by choosing said source opening between 0.1 and 0.3 cm$^2$; (v) pulsed acceleration past a fragmentation step; (vi) spatial focusing by a lens past a fragmentation step; (vii) post-acceleration of fragment ion packets past a fragmentation step; (viii) steering past a fragmentation step. Preferably, said spectral decoding step comprises a step of correlating the time variation of ion signal with said chromatographic separation, said ion mobility separation, or said mass separation.

Preferably, for the purpose of adjusting duty cycle and time width of ion packets, the method may further include one of the following steps: (i) adjusting the mean energy of continuous ion beam at said continuous acceleration step; (ii) adjusting field strength at said bunching step; and (iii) adjusting the transmitted energy spread at a step of energy filtering.

According to a third aspect of the disclosure, a method of pulsed conversion of continuous or quasi-continuous ion beams into ion packets includes the following sequential steps: (a) ionizing ions in an ion source and generating a continuous or quasi-continuous ion beam with initial energy spread under 10 eV; (b) continuously accelerating the ion beam to a mean energy being at least 10 times larger compared to the initial energy spread; (c) spatially focusing the ion beam at a plane of spatial focusing while maintaining ion angular spread within a limit so that axial ion energy spread remains comparable to the initial energy spread under 10 eV; (d) bunching the continuous ion beam with a pulsed accelerating or decelerating electric field having one boundary in time and another in space of bunching region, thus forming ion packets; (e) rejecting ions whose energies are affected by the bunching outside of the bunching boundaries; and (f) isochronously filtering of the ion packets' energy spread at chromatic deflecting or focusing of the ion packets and removing ions with unwanted energies on at least one aperture, located in the plane of spatial/angular focusing, while passing through ions, fitting the desired energy acceptance.

Preferably, the step of isochronous energy filtering may include a step of ion packet skimming by an aperture or a slit and a step of isochronous and chromatic ion beam focusing or deflection by one electrostatic field of the following: (i) a deflecting field of electrostatic sector; (ii) an angled reflecting field of a gridless ion mirror; (iii) a deflecting field of at least one pair of deflectors; (v) a periodic spatial focusing field of a periodic lens; (vi) a focusing field of at least one chromatic lens; and (vii) a combination of the above fields. Preferably, for the purpose of increasing the conversion efficiency, the step of ion pulsed bunching may be arranged at pulsing periods between 10 μs and 100 μs; and may further include a step of encoding the bunching pulses with mostly unique time intervals for subsequent decoding of partially overlapped packets of ions with different m/z.

In some implementations, bunching step is accomplished grid-free electrodes. The grid-free electrodes are optionally embodied as a set of ring electrodes with uniform distribution of a pulsed accelerating field or a pair of large diameter electrodes.

According to a fourth aspect of the disclosure, a time-of-flight mass analyzer may include an ion source, an acceleration stage, a buncher, an energy filter, a time-of-flight mass separator, and a time-of-flight detector. The ion source may be continuous or quasi-continuous. The acceleration stage is arranged to accept an ion beam emitted by the ion source. The buncher is arranged to accept an accelerated ion beam from the acceleration stage. The buncher also forms ion packets from the ion beam. The energy filter accepts ions from the buncher and isochronously removes a portion of the ions. The time-of-flight mass separator is arranged to accept ions that pass through the energy filter and to time-separate the accepted ions. The time-of-flight detector resides within or at the end of the time-of-flight mass separator. The time-of-flight mass separator has an associated energy acceptance level, and the energy filter removes ions outside of the energy acceptance level of the mass separator.

Implementation of this aspect of the disclosure may include one or more of the following features. In some implementations, the buncher is formed between a first electrode and a parallel second electrode, and the buncher has a capacitive and resistive divider to generate a nearly uniform pulsed electric field between the two parallel electrodes. The analyzer optionally further includes a spatially-focusing lens that is constructed to focus a width and a divergence of ions within the ion beam and is arranged to accept the ion beam after the acceleration stage. Optionally, the spatially-focusing lens shares electrodes with or is incorporated into at least one of the ion source and the acceleration stage.

In some examples, the analyzer further includes a suppressor arranged as a field-fee region upstream of the buncher and a pulse generator applies a pulsed voltage to the suppressor. Optionally, the suppressor includes an electrode arranged to steer approaching ions, and a single pulse generator applies the pulsed voltage to the suppressor and to one of two parallel electrodes forming the buncher. Additionally, the suppressor optionally includes a bipolar mesh to push and deflect ions.

In some implementations, the time-of-flight mass separator is embodied as either a singly reflecting time-of-flight mass spectrometer or a multi-reflecting time-of-flight mass spectrometer. And, in some implementation, the buncher optionally includes two parallel electrodes and a pulsed generator providing a pulsed voltage to one of the two parallel electrodes. Or the buncher optionally includes grid-free electrodes forming an electrostatic field.

The energy filter optionally forms an isochronous curved inlet to the time-of-flight mass separator. The energy filter optionally includes a planar lens, a first electrostatic sector, a second electrostatic sector, a third electrostatic sector, a set of surrounding slits, and an energy filtering slit. The planar lens is arranged to spatially focus ion packets in a horizontal direction. One slit of the set of surrounding slits is located at the entrance and at the exit of each electrostatic sector. The energy filtering slit provides energy-level-based removal of outlier ions. Additionally, the energy filter optionally includes a separating slit and at least one of: angled ion mirrors, an electrostatic sector, deflectors, and one or more lenses.

The analyzer optionally includes a gaseous radio frequency ion guide, an axial DC field, a shield electrode, and an extraction electrode. The gaseous radio frequency ion guide is arranged to provide collisional dampening of an incoming ion beam. A combination of the shield electrode and the extraction electrode provide a field of spatial ion focusing.

In some implementations, the ion source is embodied as a closed EI ion source accepting sample from a gas chromatograph and having an ion chamber, a repeller connected to a pulse generator, and an extractor connected to a pulse generator (114e). In some example, the ion source includes an accumulating ion guide formed by multipole rods, an auxiliary push electrode receiving periodic soft extraction pulses, an auxiliary DC trap electrode, and an exit skimmer receiving periodic soft extraction pulses. The analyzer optionally includes a differential pumped tube and an isochronous curved inlet to the time-of-flight mass separator formed by the energy filter. The differential pumped tube receives ion packets from the buncher and passes the ion packets into the isochronous curved inlet.

The time-of-flight detector optionally includes a conductive converter, at least one magnet, a positively-biased scintillator, and a seal photomultiplier. The conductive converter receives ion packets from a drift space of the time-of-flight mass separator. The conductive converter has a potential that has a negative charge differing from the negative charge of a potential of the drift space. The at least one magnet forms a magnetic field deflecting electrons reflected by the conductive converter. The positively-biased scintillator has a conductive mesh coating or covering and accepts electrons deflected by the magnetic field. The sealed photomultiplier resides downstream from the positively-biased scintillator.

The analyzer optionally comprises a time ion selector, a fragmentation cell, a fragmented ion mass analyzer, and a pulse generator. The time ion selector accesses parent ions separated in the time-of-flight separator. The fragmentation cell accepts the parent ions from the time ion selector. The fragmented ion mass analyzer accepts fragmented ions from the fragmentation cell. The pulse generator connects to the time ion selector. Both the time-of-flight separator and the fragmented ion mass analyzer are embodied as either a singly reflecting time-of-flight mass spectrometer or a multi-reflecting time-of-flight mass spectrometer.

Overall, there are proposed apparatuses and methods for time-of-flight mass spectrometry to enable effective pulsed conversion of continuous ion beams into pulsed ion packets. Bunching of energetic continuous ion beams forms ion packets, filtered by a subsequent isochronous energy filter. The bunching method is particularly suitable for ion sources with relatively large spatial emittance, not fitting an acceptance of orthogonal accelerators. The method is particularly suitable for MR-TOF MS, which accommodates small-sized ion packets and where the duty cycle advantage of orthogonal accelerators is minor.

The details of one or more implementations of the disclosure are set forth in the accompanying drawings and the description below. Other aspects, features, and advantages will be apparent from the description and drawings, and from the claims.

DESCRIPTION OF DRAWINGS

Various embodiments of the present invention together with arrangement given illustrative purposes only will now be described, by way of example only, and with reference to the accompanying drawings in which:

FIG. 7 presents an electrode and simulated ion trajectories with a curved energy filter and simulated histograms for energy and time distribution past the curved energy filter;

FIG. 8 depicts schematic view of alternative energy filters;

DETAILED DESCRIPTION

Orthogonal Acceleration in MR-TOF MS

Figure 1:
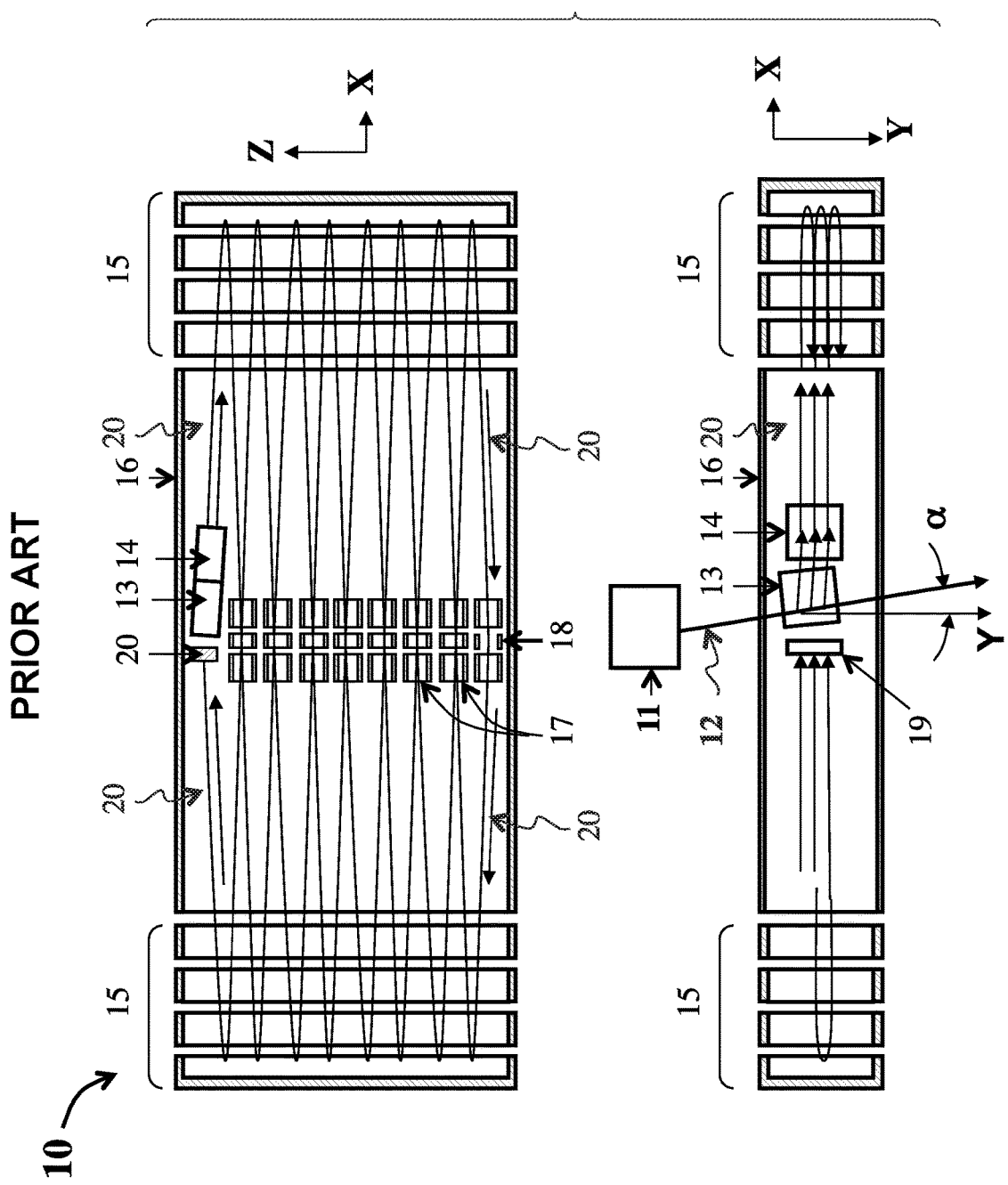
FIG. 1 depicts top and side schematic views of a multi-reflecting time-of-flight mass spectrometer with an orthogonal accelerator similar to WO2007044696.

Referring to FIG. 1, an embodiment 10 of a MR-TOF MS utilizing an orthogonal accelerator (OA) 13 of WO2007044696, which is incorporated herein by reference, comprises a continuous ion source 11, the OA 13 with a steering lens 14, a pair of parallel and gridless ion mirrors 15 separated by a negatively floated drift space 16, a periodic lens 17 with a steering deflector 18, and a detector 19. In operation, a well-directed continuous ion beam 12 is introduced into OA substantially along the Y-axis. Periodic pulses (not shown), which are applied to plates of the OA 13, accelerate ion ribbon packets into the drift space of the MR-TOF MS and along a jigsaw trajectory 20. At the OA 13, the trajectory of the ion beam is offset from the Y-axis at a small angle α, which enables compensation for time-of-flight aberrations at ion beam steering, while using a finite energy level for the ion beam 12 between 20 eV and 100 eV.

Practical implementations of the scheme illustrated in FIG. 1 limit the Y-length of ion packets to approximately 5-6 mm (corresponding to a 600 mm cap-to-cap distance) in order to maintain low cross time-of-flight absolute aberrations T|YYK in relation to both the vertical size and the energy spread. Another challenge is in maintaining the continuous ion beam 12 as a narrow beam in both the X-direction (as narrow as 1-1.5 mm) and the Z-direction (as narrow as 2-3 mm), which may require using a heated collimator (not shown) with two slits in order trim a portion of continuous ion beam 12. Then a strong accelerating field of 200 V/mm would allow dropping so-called turnaround time to 3-4 ns while not yet exceeding energy acceptance of the MR-TOF analyzer (300 eV at 4 kV acceleration). Any attempt of reducing the width of the ion beam 12 causes very rapid loss of signal intensity. As an example, reducing the width of the ion beam 12 twice (for a twice-shorter turn-around time and a twice-higher resolving power) would cause a 16-fold loss of intensity, since both apertures of the heated collimator have to be reduced twice and the phase acceptance of the collimator drops as a fourth power of the aperture size. Thus, the scheme of FIG. 1 is rigid and resistant to adjustment of the resolving power, and the compromises between sensitivity and resolution are unfavorable.

The scheme of FIG. 1 works well when confining the continuous ion beam 12 with a collisional dampening in an RF-only quadrupole. However, if attempting to utilize an ion sources with large ion currents above 10 nA in for this scheme, the beam emittance expands due to space charge effects in the RF-only quadrupole, and transmission rapidly drops.

Bunching and Pulsed Acceleration of Ion Packets

Bunching of ion packets is well-described in nuclear physics, usually following a chopping of iso-mass continuous ion beams. Bunching (i.e. pulsed acceleration or deceleration with one boundary—start or end—being in time and another at constant distance—mesh or annual electrode) provides time-refocusing of ion packets while conserving temporal emittance (i.e. the product $\Delta T^* \Delta K$ of the time spread $\Delta T$ and the energy spread $\Delta K$). The fundamental ion optical property is known as the Liouville theorem. Focusing/defocusing properties of bunching can be observed in distance-time diagrams.

Figure 2:
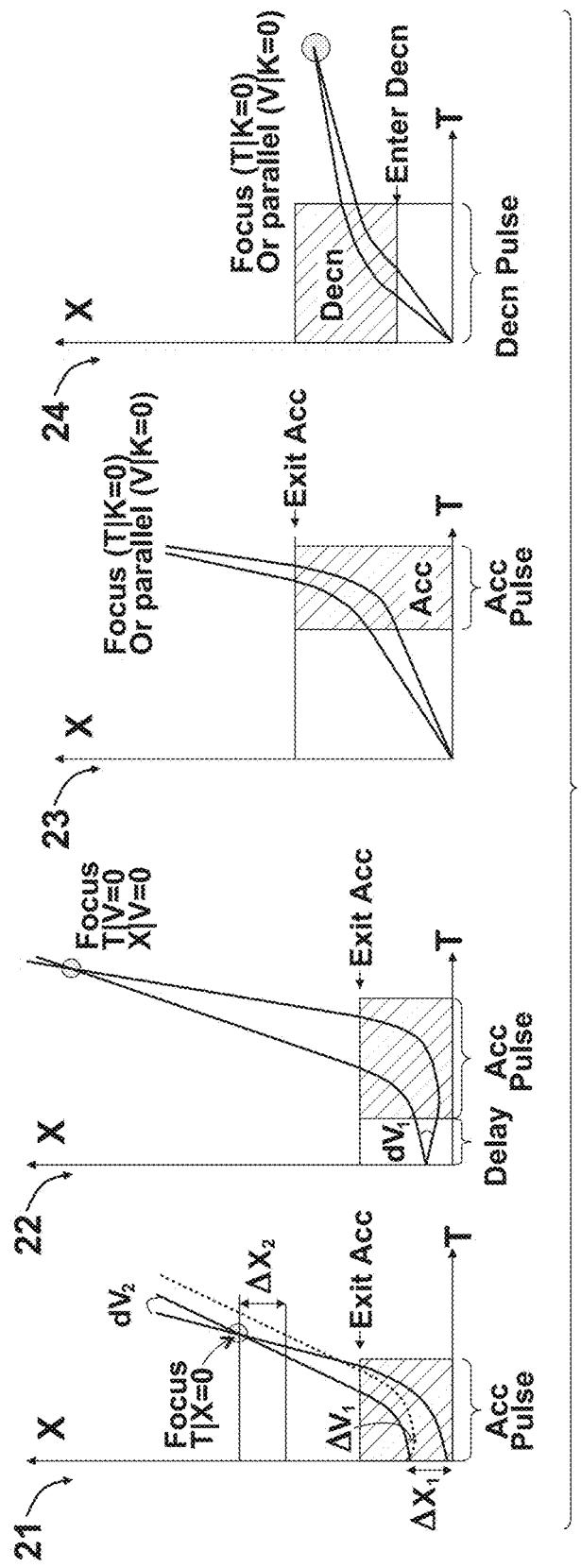
FIG. 2 depicts time-space diagrams of known bunching and pulsed acceleration methods.

The same fundamental law of conserving temporal emittance is also true for pulsed acceleration schemes, applied to initially stagnated ion clouds. Referring to FIG. 2, several bunching and pulsed acceleration schemes are depicted, with distance plotted along an X-axis and time along a T-axis. Scheme 21 corresponds to pulsed acceleration of ions at zero average velocity (e.g. in orthogonal accelerator). Acceleration starts at T=0 and ends when ions exit an acceleration region. The initial spatial spread $\Delta X_1$ gets converted into a velocity spread $\Delta V_2$. Though temporal focus T|X=0 is achieved after twice longer distance, still, initial velocity spread $\Delta V_1$ inevitably causes some finite packet width $\Delta X_2$. The product of the spatial spread and the velocity spread is conserved (i.e. $\Delta V_1 ^* \Delta X_1 = \Delta V_2 ^* \Delta X_2$). The same product is also conserved in a more convenient form (i.e. $\Delta T^* \Delta K$), and turn-around time $\Delta T_2 = \Delta X_2/V_2$ may be decreased by using a higher-strength acceleration field, E, (at higher acceleration A=qE/m) only at the expense of increased energy spread: $\Delta T_2 = \Delta V_1/A = \Delta V1^*m/qE$; and $\Delta K_2 = \Delta X_1 ^* E$. Additionally, the conversion coefficient between two forms of the conserved product is:

$$\Delta T_1 ^* \Delta K_1 = \Delta T_2 ^* \Delta K_2 = \Delta V_1 ^* \Delta X_1 ^* m/q = \Delta V_2 ^* \Delta X_2 ^* m/q \quad \text{(Equation 1)}$$

Scheme 22 corresponds to a so-called delayed extraction (Willey McLaren' 1953), wherein an initially stagnated ion cloud is allowed to expand, and the acceleration pulse is applied with a delay. The scheme allows reaching temporal focusing T|V=O, and either reducing turnaround time or moving a time-focal plane. However, it is fundamentally impossible to simultaneously reach similar focusing for the initial spread for the same reason: $\Delta T^* \Delta K$=const.

Scheme 23 corresponds to the delayed extraction in MALDI sources, providing bunching of ion packets with non-zero average velocities. Scheme 24 provides corresponding focusing at a deceleration region. Multiple other schemes with accelerating or decelerating bunching exist to provide either temporal focusing, focal-plane adjusting, packets with reduced-energy-spread packets obtaining (known as debunching in nuclear physics) when acceleration or acceleration have different boundaries—one at a fixed time and another at a fixed position.

The statement of conserving temporal emittance seems to be in contradiction with recently proposed simultaneous spatial and velocity focusing in U.S. Pat. No. 8,461,521. However, the claimed simultaneous focusing is achieved for the second order time per energy aberration T|KK (also achievable in dual stage ion mirrors) and not for the first order aberration T|K.

Let us highlight several important features of ion packet bunching:

The product $\Delta T^* \Delta K$ is conserved and is related to the product $\Delta X^* \Delta V$;

Bunching can operate with either acceleration or deceleration;

Bunching can be used for time-focusing, for time focus adjustment, or for reducing energy spread;

In a sense, bunching focuses ion packets in X-T space, similar to spatial lens focusing with one difference—bunching can also be used for defocusing, while lens are limited to focusing;

Reduction of the time spread $\Delta T$ is enabled, but comes at the expense of an increased energy spread $\Delta K$, which is reasonable until hitting the energy acceptance of the TOF analyzer (15-20% in TOF and 7-10% for MR-TOF); and The full mass range is preserved only if ion packets have zero average velocity (illustrated in schemes 21 and 22), otherwise bunching causes mass range reduction (sometimes desirable).

Axial Bunching for Continuous Ion Beams

Also, versions of bunching for continuous ion beam conversion to pulses at a limited duty cycle have been presented (for example, in U.S. Pat. No. 5,614,711 (Heftje) and U.S. Pat. No. 7,045,792 (SAI), each of which are incorporated herein by reference), though the proposed methods limit mass range, produce an excessive energy spread, and form parasitic TOF peaks. This disclosure alleviates some of these problems existing in the presented versions of axial bunching methodology.

Figure 3:
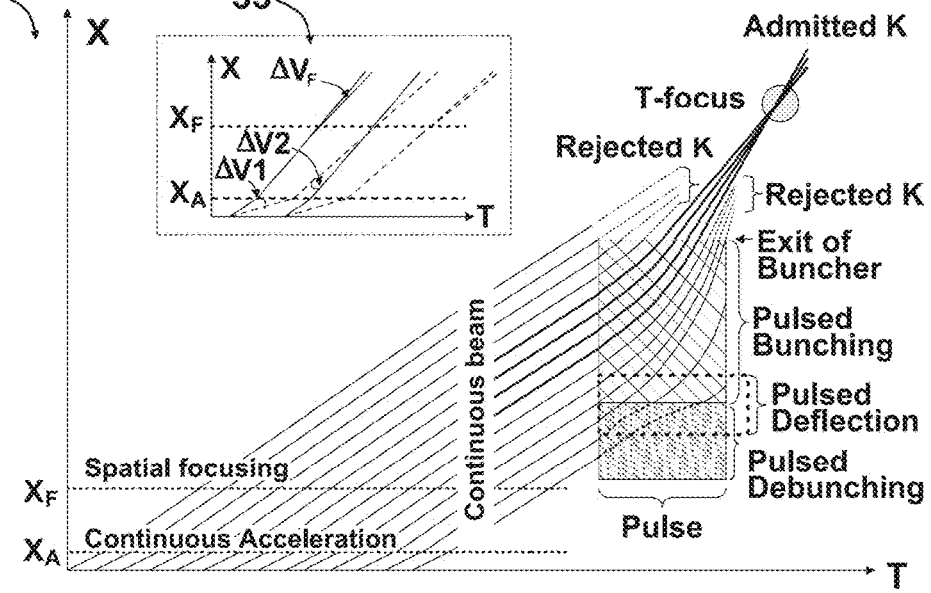
FIG. 3 depicts block diagram and time-space diagram of bunching method.

Referring to FIG. 3, on a level of block schematic a method 31 of the present invention is disclosed for pulsed conversion of continuous or quasi-continuous ion beams into ion packets. The illustrated method 31 includes the following sequential steps: (a) ionizing ions in an ion source and generating a continuous or quasi-continuous ion beam with an initial energy spread under 10 eV; (b) continuously accelerating the ion beam to a average energy being at least 10 times larger than the initial energy spread; (c) optionally, spatially focusing the ion beam at a plane of spatial focusing while maintaining ion angular spread within a limit so that axial ion energy spread remains comparable to the initial energy spread; (d) bunching the continuous or quasi-continuous ion beam with a pulsed accelerating or decelerating electric field having one boundary in time and another in space, thus forming ion packets; (e) rejecting ions whose energies are affected by the bunching outside of the bunching boundaries; and (f) isochronously filtering the energy of the ion packets at chromatic deflecting or focusing of said ion packets and removing ions with unwanted energies on at least one aperture, located in the plane of spatial/angular focusing, while passing through ions, fitting the energy acceptance of the subsequent time-of-flight mass analysis step. Additionally, the illustrated method 31 includes the following sequential steps, which refer more generally to the TOF MS analysis (rather than specifically to the pulsed conversion of continuous or quasi-continuous ion beams into ion packets process): (g) separating the ion packets in time along isochronous reflections (which may be single of multiple) in an electrostatic field of at least one ion mirror; (h) detecting the ion packets with a time-of-flight detector to form a waveform signal; and (i) analyzing the detected waveform signal to extract mass spectral information. Of the steps listed above, (c), (g), (h), and (i) are shown in brackets to stress that these are optional or additional steps that may occur as part of the overall method but are not directly related to the pulsed conversion.

Again referring to FIG. 3, the method 31 of pulsed conversion is presented using a distance-time diagram 32 for ions of a single mass. Ions trajectories, plotted along an X-axis and a T-axis, start at T=0 with relatively small velocities, corresponding to a small inclination angle within the X-T plane. The drawing trims the trajectories with negative X-values in order to focus upon steps occurring at T≥0.

The Continuous Acceleration Step: Occurs at constant $X_A$ region and results in an increased ion velocity, which corresponding to a larger inclination angle in diagram 32. Ions are accelerated to an average energy $K_C$ that is at least 10 times greater than the energy spread $\Delta K_C$, which becomes important for the success of subsequent steps. Multiple mass-spectrometric continuous ion sources are known to generate ion beams with energy spreads of a few electron volts or, if special care is taken, as low as 1 eV or less. For example, the axial energy spread is known to be dampened under 1 eV with use of gas-filled RF-only ion guides. Such energy spread is still too large for TOF MS and would require a field strength of more than 1 kV/mm to reduce the turnaround time to under 5 ns for 1000 amu. Continuous acceleration reduces absolute velocity spread. For example, accelerating the mean velocity from $V_1$ to $V_2$ drops velocity spread according to:

$$\Delta V_2 = \Delta V_1 * V_1/V_2 \quad \text{(Equation 2)}$$

Equation 2 is illustrated in the diagram 32 by the reduction of the spread of inclination angles following the continuous acceleration plane $X_A$. For ion clouds with zero mean velocity (i.e. $V_0=0$) and thermal energy $K_0$ corresponding to $2\Delta V_0$ velocity spread, where $V_0=(2K_0q/m)^{0.5}$, the continuous acceleration to energy $K_C$ reduces the velocity spread as $2\Delta V_C=(2q/m)^{0.5}*[(K_C+K_0)^{0.5}-(K_C-K_0)^{0.5}]$, thus, full velocity spread $2\Delta V_C$ after continuous acceleration becomes:

$$2\Delta V_C = \Delta V_0 * (K_0/K_C)^{0.5} \quad \text{(Equation 3)}$$

Acceleration of ion cloud with 0.5 eV thermal energy (1 eV full energy spread) to 1000 eV energy allows substantial velocity spread reduction (i.e. reducing velocity spread by 60 times). Though continuous acceleration does not improve the converter's duty cycle (as shown below in Table I), it does allow using practically convenient sizes and pulse amplitudes of the bunch converter, and it reduces chromatic aberrations by the spatially focusing lens at the next step. Thus, for a typical $\Delta K_C$ (i.e. approximately 1 eV), the method is suited for $K_C > 10$ eV and, preferably, for $K_C$ between several hundred to thousands of electron-Volts.

This reduction of absolute velocity spread is an advantage of the present disclosure. This reduction is a result on the novel apparatus and method presented herein.

The Spatial Focusing Step: Optionally, the method 31 as illustrated in diagram 32 includes a step of spatial focusing. The optional spatial focusing step adapts the ion beam width and divergence prior to the steps of bunching, time ion selection, energy filtering, and mass analysis in a TOF MS or MR-TOF MS. The spatial focusing step occurs after the continuous acceleration step to minimize chromatic aberrations at lens focusing, but the spatial focusing step occurs before bunching step in order to minimize axial velocity spread and turnaround time. The spatial focusing focuses the beam into an energy selecting aperture, resulting in an enhancement to the energy filtering step.

At the spatial focusing step, the ion beam parameters are adjusted to accomplish optimal coupling of ion packets with acceptance of the energy filter and TOF analyzer. For example, the spatial focusing may accomplish long focal lengths and small deflection angles α to avoid any significant impact that may otherwise occur to the axial energy spread of the continuous ion beam (for example, due to a large angle α which would increase the energy spread according to: $\Delta K' = K * \alpha^2$) relative to the initial energy spread $\Delta K_0$. Icon 32 shows an additional spread of axial velocity $\Delta V_F$ that is smaller than $\Delta V_2$ velocity spread in the continuous ion beam. Spatial focusing of an isoenergetic beam is an additional advantage of the novel method and apparatus of this disclosure.

The Bunching Step: After the spatial focusing step, a bunching electric pulse is applied within a space-time region known as a bunching regions that is illustrated on the diagram 32 as an accelerating pulse. Ions within the bunching region will gain ion energy proportional to the accelerating path and will be time-focused as described and illustrated in scheme 21 of the orthogonal accelerator.

The Energy Filtering Step: Bunched ion packets are later separated from the continuous ion beam by using an additional energy filter (not shown on the diagram 32). On the diagram 32, the filtered ion packets are denoted with "rejected K" for trajectories with an inclination angle that is either too large or too small. This same energy filter also allows for the removal of ions with an excessive energy spread. The removal of excessive energy-spread ions is important because those removed ions may not comply with the energy acceptance range of the subsequent TOF analyzer (also not shown on the diagram 32), which is normally 15-20% in singly-reflected gridded TOF and 7-10% in gridless MR-TOF. This allows an independent control of the accelerating field strength. For example, a strong applied pulsed acceleration may reduce the packets' turnaround time.

This energy filtering step presents a core feature of the novel method and apparatus of this disclosure. Contrary to U.S. Pat. No. 5,614,711 (Heftje) and U.S. Pat. No. 7,045,792 (SAI), the energy filtering step of the present invention eliminates unwanted ions and allows keeping an ideal portion of accelerated pulsed packet with a controlled energy and time spread. The time spread may be brought well under ins, being limited by (a) aberrations associated with the energy filtering step (which, in turn, depend on the beam size); and (b) compromised duty cycle. Removal of "bad" ions with wrong energies or originating from buncher boundaries, allows forming controlled fine ion packets.

The Eliminating Decelerated Ions Step: Such step would not be necessary if only chopping an ion beam of a single mass as in nuclear physics experiments. This step would be also unnecessary if a narrower energy range is selected that inherently excludes decelerating ions. However, TOF MS analysis deals with wide mass ranges of at least 10:1. Within the range of different masses that may occur in TOF MS analysis, inclination angles may differ by at least factor of 3. As such, it becomes unpractical to arranging pulse duration to avoid "ghost peaks" for the lighter fraction of ions within the TOF MS analysis range.

To understand the nature of these "ghost peaks" it is advantageous to analyze the particular bunching case depicted in the diagram 32 wherein the accelerating pulse is applied to the entrance electrode. In that bunching case, a pulsed decelerating field appears in front of the entrance electrode, causing a deceleration of ions as they approach the entrance electrode. The diagram 32 depicts a hashed region of "pulsed debunching". Most of the ions in this region will be decelerated and filtered by an energy filter. However, a portion of ions will experience deceleration followed by acceleration, which creates a scenario in which the ions may not be filtered by the energy filter. These decelerated-but-not-filtered ions later form "ghost peaks" during the TOF MS analysis.

Removal of those "ghost peaks" is optionally accomplished in a number of way including: the use of a separate timed ion selector; or the incorporation of such a time selection into deflecting or defocusing properties of pulsed electrode itself. For example, ions may be defocused while passing the electrode aperture, or they may be spatially deflected by an additional deflector incorporated into the pulsed electrode. In one particular embodiment a bipolar mesh could be used for both bunching and deflecting purposes if applying asymmetric pulse (for example, if the pulse is applied only to even wires). Alternatively, the decelerating field (shown as the hashed region in the diagram 32) can be removed by applying the same pulse voltage to an electrode preceding the pulse electrode. Because multiple optional methods exist for ghost-peak removal, the more generic step of removing temporally decelerated ions is not referred to as simply "deflection", "time selection", or not even "avoiding decelerated fields". Alternatively, ghost ions may be removed if a relatively narrower energy range is selected for the ion packets. But, this would result in a compromise to the bunch's duty cycle.

As described in the following, when applied to singly reflecting TOF, the method 31 has a lower duty cycle than the orthogonal acceleration method (of, for example, SU1681340). However, the method 31 provides a comparable duty cycle in the case of MR-TOF, and the method 31 provides much larger spatial acceptance in both TOF MS and MR-TOF MS. Accordingly, the method 31 may improve the overall efficiency of the pulsed conversion.

Duty Cycle at Axial Bunching

Equation 4 demonstrates the effectively used time interval for the continuous ion beam (converted into ion packets) fitting the TOF MS energy acceptance. Equation 4 assumes an energy spread of the continuous ion beam of $2\Delta K_0=1$ eV, a TOF energy acceptance of $\Delta K=350$ eV ($\Delta K/K=7\%$ and $K=5$ kV), and a target peak width of $\Delta T=3$ ns at 1000 amu. Based on the theorem of conserving temporal emittance, the effectively used time of axial bunching is:

$$T_{EFF}=\Delta T^*\Delta K/2\Delta K_0 \approx 1 \text{ µs} \quad \text{(Equation 4)}$$

Tolerating a larger peak width $\Delta T$, using larger TOF energy acceptance, or reducing ion energy spread in gas filled ion guides will increase the effectively used time $T_{EFF}$. Note that this effectively used time $T_{EFF}$ is independent of the ion energy of continuous ion beam $K_C$. This independence assumes proper adjustments of the field strength E at the pulsed acceleration buncher. Table 1 demonstrates the independence of the effectively used time $T_{EFF}$ from the continuous beam's ion energy level $K_C$ at the following elemental condition: $2\Delta K_0=1$ eV, $\Delta K=350$ eV, and $\Delta T=3$ ns for 1000 amu ions. Notably, the numbers in Table 1 are rounded:

TABLE 1

| $K_c$ (eV) | $V_c$ (mm/µs) | $\Delta V_c$ (mm/µs) | E (V/mm) | $\Delta T$ (ns) | $\Delta K$ (eV) | $X_{EFF}$ (mm) | $T_{EFF}$ (µs) |
|---|---|---|---|---|---|---|---|
| 10 | 1.41 | 0.071 | 240 | 3 | 350 | 1.5 | 1 |
| 100 | 4.47 | 0.022 | 76 | 3 | 350 | 5 | 1 |
| 1000 | 14.1 | 0.007 | 24 | 3 | 350 | 15 | 1 |

The Calculations of Table 1: The mean velocity in the continuous ion beam is calculated as $V_C=(2U_C^*q/M)^{0.5}$. The velocity spread $\Delta V_C$ is calculated with the formula provided in (Equation 3). The required strength of bunching field E is calculated to keep the turnaround time constant at $\Delta T=\Delta V_C^*M/qE=3$ ns. The energy acceptance is taken as a constant ($\Delta K=350$ eV). The effective length of the bunched ion packet is calculated as $X_{EFF}=\Delta K/qE$, and the effectively used time is calculated as $T_{EFF}=X_{EFF}/V_C$. In all cases, the accelerated field strength is adapted to keep the constant energy spread at 350 eV and the constant turnaround time at 3 ns. The effectively used time is thus calculated as 1.06 µs (shown as approximately 1 µs in Table 1), independent of the varying of the average ion energy of the continuous ion beam. For multiple reasons described below, the optimal energy turns out to be around 1 keV, which corresponding to an effective accelerating length of 15 mm, which is practically convenient.

The duty cycle of the axial bunching appears ineffective when the bunching is utilized for a standard singly reflecting Re-TOF MS. For obtaining resolution in excess of 10,000, Re-TOF MS employ typical flight times of $T=100$ µs for 1000 amu ions. Then the axial bunching provides $DC=T_{EFF}/T=1\%$ duty cycle, while an orthogonal acceleration method (for example, SU1681340) is known to provide 10-15% duty cycle due to wide spatial acceptance of Re-TOF, which permits 25-40 mm long orthogonal accelerators (OA). The axial energy of continuous ion beams is usually chosen approximately 50 eV for effective ion transfer into OA. So the axial velocity of 1000 amu ions is 4.5 mm/µs, and an effective time for OA is $T_{EFF}=5-10$ µs, which is notably larger than $T_{EFF}=1$ µs associated with the axial bunching method 31 for Re-TOF MS.

However, the conclusion (regarding resolution) is quite different, when the axial bunching method 31 is utilized for MR-TOF analyzers, accommodating short ion packets under 5-6 mm. In such cases, the effective time of OA drops to between 1-1.2 μs (for 1000 amu ions), and the gain associated with OA axial bunching disappears. In fact, the OA method becomes particularly disadvantageous, when using ion beams with large spatial emittance, such as EI sources or glow discharge sources. In such a case, the utilization of OA requires ion beam collimation accompanied by large spatial losses and strongly reduced overall converter efficiency. As shown below, the method of axial bunching allows adopting ion sources with exceptionally wide emittance and energy spreads, which is poorly compatible with the OA method.

The realization presented herein is striking. Axial bunching has been considered to have a far inferior duty cycle compared to that of orthogonal acceleration. This disclosure presents evidence to the contrary.

Spatial Acceptance and Advantages of Axial Bunching

The gain attributed to the axial bunching method 31 over the OA scheme are further illustrated by the improvement of both the overall spatial acceptance (A), which is demonstrated in Equation 5, and the product of the spatial acceptance and the effectively used time ($A*T_{EFF}$), which characterizing the overall efficiency of pulsed converters, where:

$$A=(\Delta X*\Delta V)^2=(\Delta X*\Delta a)^2 *K \quad \text{(Equation 5)}$$

The one dimensional OA acceptance (a) is approximately a=2 mm*deg at 50 eV energy, and, thus, full acceptance is A=200 mm$^2$*deg$^2$*eV=0.05 mm$^2$rad$^2$eV.

Estimates for acceptance of MR-TOF are:
a=2.5 mm*deg at 5 keV (being more precise: 5 mm*1 deg in a vertical Y-dimension and 3 mm*0.4 deg in the Z-direction); and
A=30,000 mm*deg$^2$*eV≈10 mm$^2$rad$^2$eV.

Estimates for Re-TOF MS are:
a=10 mm*deg at 10 keV (i.e. A=1E+6 mm*deg2*eV≈300 mm2 rad2 eV).

Previously the effective time of OA was estimated as $T_{EFF}$=10 μs in TOF MS and as $T_{EFF}$=1-1.5 μs in MR-TOF MS. Utilizing the axial bunching method 31, the $T_{EFF}$=1 μs. The results are presented in the Table 2, which illustrates that spatial acceptance of the OA is significantly smaller than that of TOF and MRTOF analyzers:

TABLE 2

| Full Spatial Acceptance (A) | | | |
|---|---|---|---|
| | a (mm$^2$*deg) | K (eV) | A (mm$^2$*rad$^2$*eV) |
| OA | 2 | 50 | 0.05 |
| MR-TOF | 2.5 | 5,000 | 8 |
| Re-TOF | 10 | 10,000 | 300 |

Contrary to common perception, the overall efficiency—characterized by the product $A*T_{EFF}$—is notably higher in axial bunching Vs OA. For MR-TOF MS, $A*T_{EFF}$=10 mm$^2$rad$^2$eV*μs with axial bunching, while $A*T_{EFF}$=0.08 mm$^2$rad$^2$eV*μs with OA. For Re-TOF MS, $A*T_{EFF}$=300 mm$^2$rad$^2$eV*μs with axial bunching, while $A*T_{EFF}$=0.5 mm$^2$rad$^2$eV*μs with OA. The results are presented in the Table 3, which also shows the efficiency gain of the axial bunching method 31 compared to the OA scheme when employing ion sources with wide emittance, such as EI, SIMS, and glow discharge. Axial bunching provides multiple other technical advantages and convenient schemes (not available for OA scheme), such as easily controlled signal gain for wider dynamic range, selection of narrow mass ranges, and built in MS-MS features—all of which are described below.

TABLE 3

| Overall Efficiency ($A*T_{EFF}$) of Axial Bunching (A × B) and OA | | | |
|---|---|---|---|
| | $A*T_{EFF}$ for OA (mm$^2$*rad$^2$*eV*μs) | $A*T_{EFF}$ for AxB (mm$^2$*rad$^2$*eV*μs) | A × B Gain |
| MR-TOF MS | 0.08 | 10 | X 100 |
| Re-TOF MS | 0.5 | 300 | X 600 |

The data in Tables 2 and 3 highlight the differences between the novel method 31 of axial bunching and conventional method of the orthogonal acceleration. In orthogonal accelerators, spatial emittance of continuous ion beams does affect the turnaround time. Special efforts must be taken and ionic losses must be accepted to sustain narrow ion beams at the OA entrance. Contrary to OA, the axial bunching method 31 tolerates much wider ion beams and, for most of the common ion sources, does not require any trimming of the continuous ion beams. In addition, axial bunching allows obtaining ultra-short ion packets (for example, under one nanosecond), which are practically independent of ion beam emittance for most of the conventional ion sources. Such is a major inventive step of the method and apparatus of this disclosure.

Axial Bunching for TOF MS

Figure 4:
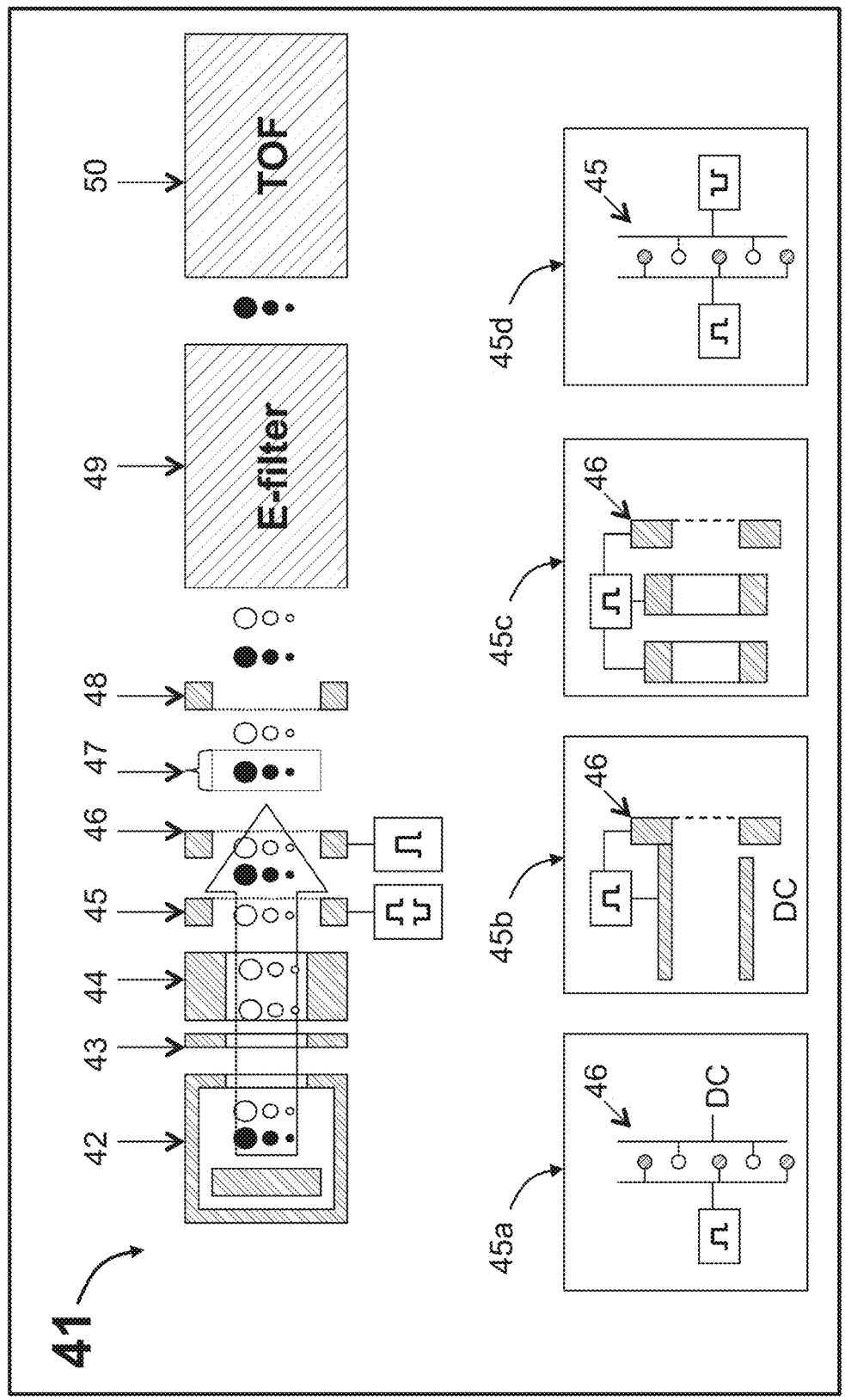
FIG. 4 depicts an embodiment of a time-of-flight mass spectrometer with bunching converter; related icons depict several suppresser embodiments.

Referring to FIG. 4, a preferred embodiment 41 of time-of-flight mass spectrometer performing the axial bunching method 31 of the disclosure includes the following sequentially and axially aligned components: a continuous source 42, a continuous acceleration stage 43 (i.e. an accelerator), a spatially focusing lens 44, a suppresser 45, a buncher formed with parallel electrodes 46 and 48, an energy filter 49, and a TOF analyzer 50, which may be either Re-TOF or MR-TOF. Pulse generators, depicted by gate icons, are connected to electrodes 45 and 46.

In operation, a suitable continuous ion source 42 generates a continuous ion beam (shown in FIG. 4 by a white arrow) with less than 10 eV energy spread ΔK, and more preferably ΔK<1 eV. The continuous source 42 generates ions in a wide mass range as presented by black circles of different size. The accelerator 43 continuously accelerates the ion beam to a mean energy $K_C$, which at least ten times larger than the energy spread ΔK. The absolute velocity spread of the continuous ion beam drops as described by (Equation 3). The spatially focusing lens 44 spatially focuses the continuous ion beam onto the energy filter 49. A low relative level energy spread is helpful to avoid chromatic lens aberrations. The spatially focusing lens 44 may be incorporated into or may share some of electrodes with the continuous source 42, the accelerator 43, and the suppresser 45. The continuous ion beam is delivered all the way to a bunching region 47 between electrodes 46 and 48.

At the bunching step, a voltage pulse on electrode 46 forms pulsed accelerating field between electrodes 46 and 48. Optionally, a set of electrodes may be used with a capacitive and resistive divider to generate a nearly uniform pulsed electric field. A portion of the continuous beam (shown by black circles) within the bunching region 47 gains a sufficient amount of energy to pass the subsequent energy filter 49. The pulse duration is chosen as a sufficiently long time period for complete clearance of the acceleration gap between electrodes 46 and 48 by the heaviest ions of interest in the continuous beam. Surrounding portions of the ion beam, illustrated as white circles, will leave the bunching region 47 at incorrect energies and, thus, will not pass the energy filter 49. Formed ion packets enter a TOF analyzer 50 for mass analysis.

Another voltage pulse is applied to the suppressor 45 to avoid temporally decelerated ions. The suppressor 45 may either retard or deflect newly entering ions, or it may simply form a field free region in front of the electrode 46. In one embodiment 45a, the suppressor 45 is combined with the pulsed electrode 46 using a bipolar mesh, which pushes ions at a far distance and deflects approaching ions. In another embodiment 45b, the bunching pulse is applied to a deflecting electrode to steer approaching ions. Yet in another embodiment 45c, the bunching pulse is applied to a set of preceding electrodes to avoid decelerating field in front of a mesh of electrode 46. Yet in another embodiment 45d, the suppressor 45 is made as bipolar mesh that deflects both upstream ions and ions in close vicinity of the bunching electrode 46.

In order to increase the duty cycle of the pulsed ejection scheme 41, preferably, the bunching pulse 46 is applied frequently (much faster than required for the heaviest ions to pass the MR-TOF analyzer) with encoded pulse intervals (EFP) as described in WO2011135477, which is incorporated herein by reference. As a numerical example, the average period of the bunching pulses may be 10 μs, and an effective time of the buncher may be 1 μs, which corresponds to a 10% time duty cycle of the pulsed conversion.

Time Focusing in an Ideal Buncher

Figure 5:
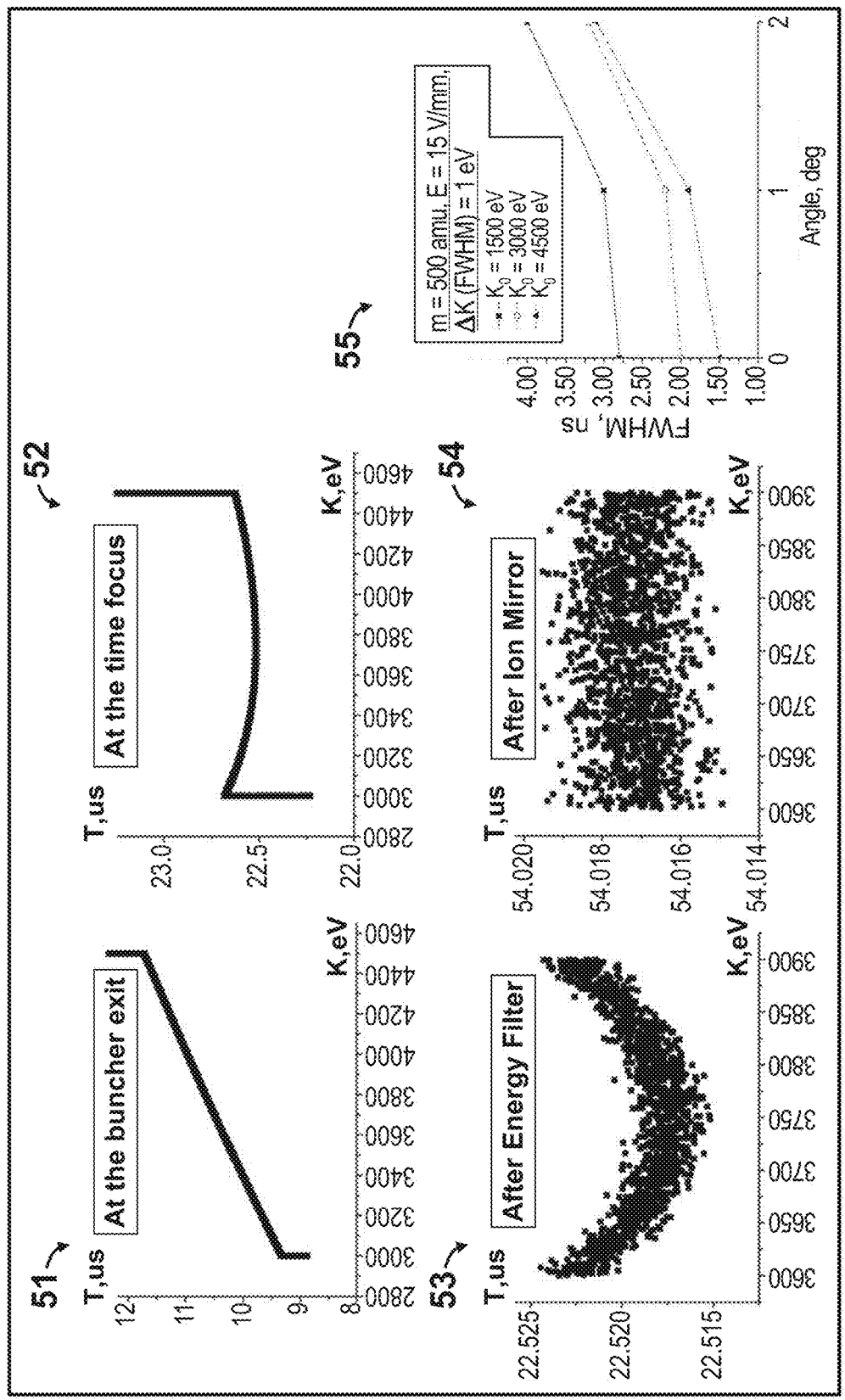
FIG. 5 shows results of ion optical simulations for ideal "grid covered" axial buncher presented in time-energy diagrams and a graph for ion packet time spread Vs ion beam angle.

Referring to FIG. 5, there are presented results of simulating an ideal bunching region 47 with a one-dimensional buncher having fine meshes. The results of FIG. 5 were determined utilizing an assumed isotropic energy spread of 1 eV within a 500 amu ion beam having 3000 eV ion energy. A 1500V pulse is applied across a 100 mrn buncher with a 15 V/mm field strength. Time-energy diagrams are presented for buncher exit (diagram 51) and at the intermediate time focus (diagram 52), which is located approximately 500 mm behind the buncher. Average ion energy is 3750 eV and average velocity is 40 mm/μs for the diagrams 51, 52. Notably, a single stage buncher introduces a T|KK aberration as seen by the quadratic curve in diagram 52. It is possible to remove the aberration illustrated in diagram 52 either by using a dual stage buncher ith a continuous acceleration stage 43 or by using a dual stage ion mirror. The beam has 1500 eV energy spread at 3750 eV mean energy (i.e. it is poorly compatible with TOF MS, that has a smaller relative energy acceptance). After filtering a 300 eV energy window by an ideal energy filter (example energy filters are described hereinafter), the ion packets continuing beyond the energy filter 49 have approximately a 10 ns time spread, primarily defined by the buncher T|KK aberration (as illustrate in diagram 53). After using a two stage ion mirror (as illustrated in diagram 54), the T|K aberration is removed and ion packet time width at a peak base stays under 4 ns with FWHM=2 ns, primarily defined by the turnaround time formed in the buncher. Note, that flat acceleration to 3750 eV of the ion beam with an energy spread of 1 eV causes only 24 mrad (1.5 degree) full beam divergence. When introducing an additional angular spread, which may be caused by an intermediate lens system forming the beam, additional velocity spread is introduced into the continuous ion beam. This introduced velocity spread is capable of causing an additional time spread (as illustrated in diagram 55). For an angular spread of less than 2 degrees (being already beyond the MR-TOF MS spatial acceptance), the buncher is capable of forming less than 3 ns FWHM pulse packets, while using 20 mm of ion beam at 40 mm/μs velocity (i.e. at 0.5 μs effective time).

Figure 6:
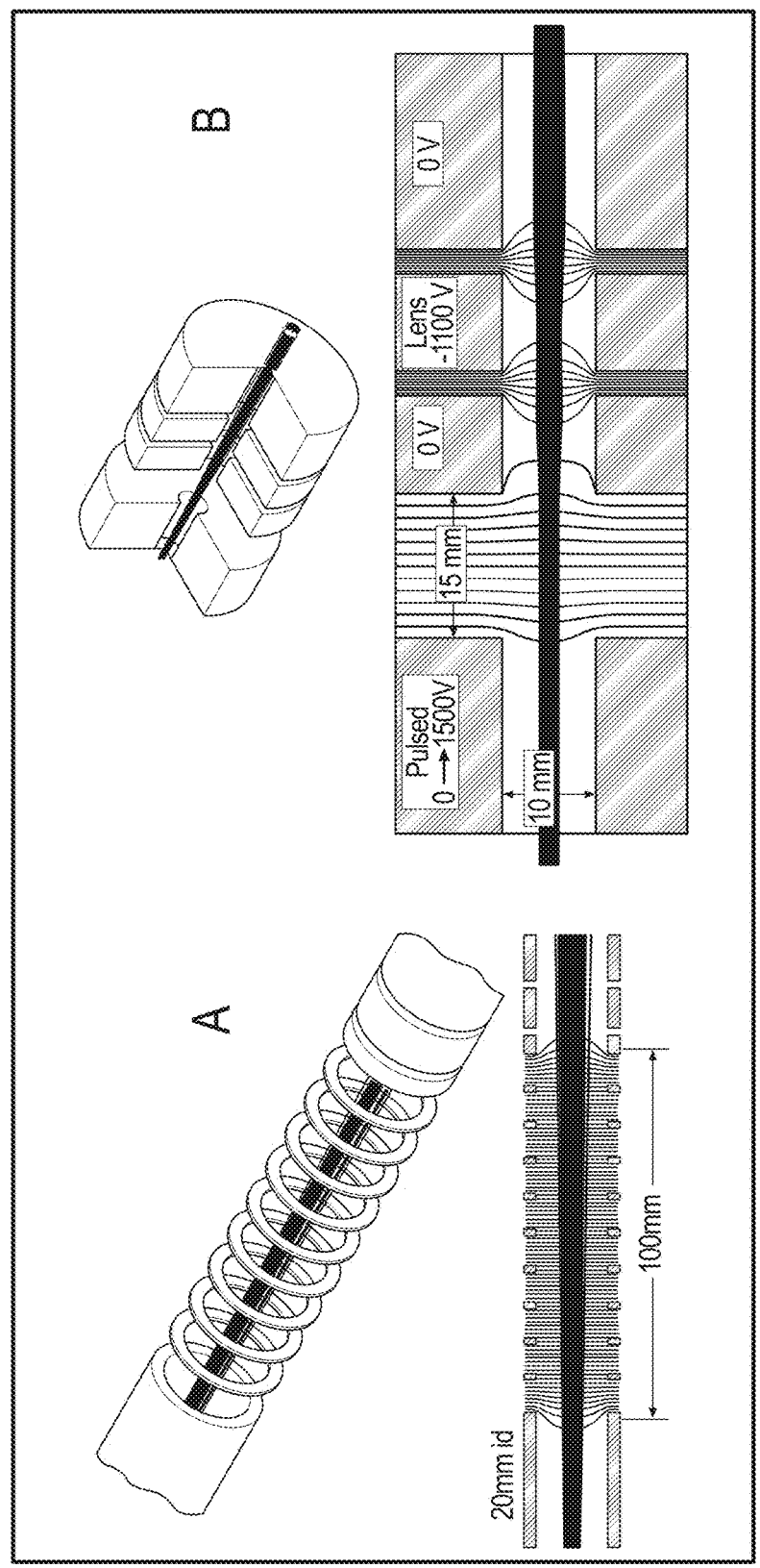
FIG. 6 shows electrode and ion trajectory view in the simulated "long" and "short" ideal buncher.

Referring to FIG. 6, in simulations, an ideal gridded buncher 41 has been replaced by grid-free electrodes. In FIG. 6A, the grid-free electrodes are embodied as a set of ring electrodes with uniform distribution of a pulsed accelerating field. In FIG. 6B, the grid-free electrodes are embodied as a pair of large diameter electrodes. In the buncher of FIG. 6A, a narrow bunched ion packet (≈2 ns) is created with a weak bunching electrostatic field strength (15 V/mm) from an energetic (3000 eV) continuous ion beam. In the buncher of FIG. 6B, a similar narrow ion packet is created with a strong field (100 V/mm) from a low energy (100 eV) continuous ion beam. Grid-free systems provide exactly the same time focusing as ideal mesh covered buncher in of FIG. 5, without any notable spatial defocusing.

To account for energy filtering, the disclosed axial buncher and method of axial bunching obtain extremely short ion packets (estimated as short as 0.1 ns for 1 mm-3 mm wide ion beams and 1-3 ns for 3 mm-10 mm ion beams). The limit is presently set by time-of-flight aberrations at the energy filtering step. Ultra-short packets for narrow beams can be reached, or very wide beams at compromised ion packet time width can be bunched.

Exemplary Energy Filter

Referring to FIG. 7A, an embodiment 71 of the pulsed converter optionally includes a closed electron impact (EI) ion source 42, an electrostatic acceleration stage 43, an axial symmetric lens 44, a gridless buncher 47 depicted between entrance section 46 and exit section 48, and an energy filter 79. The gridless buncher 47 may optionally be embodied as the buncher illustrated in FIG. 6A. The energy filter 79 comprises a planar lens 72, a first electrostatic sector 73, a second electrostatic sector 74, a third electrostatic sector 75, a set of surrounding slits 76, and an energy filtering slit 77.

The closed EI ion source 42, which is grounded, generates an ion beam with an energy spread of approximately 1 eV. After accelerating the ion beam to 1500 eV at the electrostatic acceleration stage 43 (floated to −1500V), the ion beam emittance is estimated as 2 mm*deg, based on experimental data. The axial symmetric lens 44 provides spatial focusing at a middle of the buncher 47. The entrance plate 46 pulses (i.e. alternates from −1500V to OV), and the pulse is linearly distributed between the buncher electrodes with aid of a capacitive-resistive divider (not shown in FIG. 7). The 100 mm long buncher 47 forms an accelerating field of 15 V/mm, which is similar to prior the "ideal buncher" simulations illustrated in of FIG. 5. The planar lens 72 spatially focuses ion packets in a horizontal direction to provide spatial focusing at the energy filtering slit 77. After this focusing, ions enter the first electrostatic sector 73. Then, ions having a middle energy of 2250 eV (+/−150 eV) are able to pass through the energy filtering slit 77, which may be embodied with a width of 2.5 mm. The energy filtering slit 77 cuts off the remaining ions, as illustrated by the lower left graph of FIG. 7. This corresponds to the passing of the ions which occurred at a 20 mm-long middle section of the buncher 47, and corresponds to an 0.85 μs effective time for 500 amu ions (a velocity of 24 mrn/μs).

The three electrostatic sectors 73, 74, 75 are designed to minimize time distortions while passing ions at an X|X=1 and a|a=1 transformation. The overall FWHM peak is less than 4 ns (accounting for initial energy and angular spreads), as illustrated by the lower right graph of FIG. 7. The curved energy filter 79 of the embodiment 71 of the disclosure on shown on FIG. 7 serves the purpose of energy filtering of an axial-bunched ion beams, while accepting wide ion beams and introducing only acceptable time distortions.

Alternative Energy Filtering Schemes

Referring to FIG. 8, alternative energy filters, depicted by exemplar systems 81-84, may be embodied as: angled ion mirrors 86, which are preferably gridless; electrostatic sectors 87; deflectors 88; lenses 89; or a combination of those elements. Systems 81-84 each employ spatial ion focusing at a separating slit 90 and some chromatic (i.e. energy dependent) ion optical elements which displace ions of unwanted trajectories from the center of the separating slit 90. In FIG. 8, the ions of unwanted trajectories are illustrated by dashed lines. Because subsequent TOF analyzers possess 7-10% relative energy acceptance, the energy filter systems 81-84 may have limited dispersion, may only produce minimal time distortions, and may avoid contamination by ions of unwanted energies. For example, the ion-mirror-based systems (for example, system 81) are especially prospective for these criteria.

Figure 9:
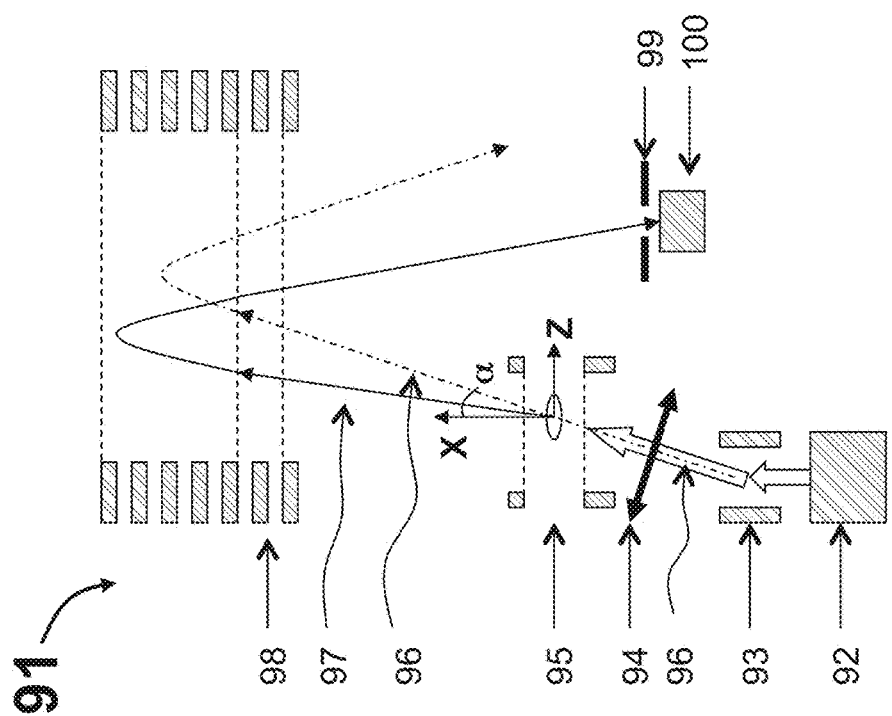
FIG. 9 depicts a schematic view of singly reflecting TOF MS equipped with axial buncher of the present invention, operating with the angled injection of continuous ion beam.

Another embodiment of the disclosure, presented as a singly reflecting TOF MS 91 with an axial bunching converter, is illustrated in FIG. 9. Referring to FIG. 9, in order to incorporate the axial bunching, the singly reflecting TOF MS 91 includes a continuous ion source 92, a spatial lens system 94, a planar buncher 95, an ion mirror 98, a slit 99, and a TOF detector 100. Additionally, the singly reflecting TOF MS 91 optionally includes a steering means 93. The steering means 93 may be embodied as an ion beam deflector. Alternatively, the singly reflecting TOF MS 91 need not include a steering means 93, in which case, the continuous ion source 92 may merely be tilted.

The continuous ion source 92 generates a continuous ion beam 96 at a set kV energy range. The planar buncher 95 is oriented substantially parallel to both the ion mirror 98 and said detector 100. The continuous ion beam 96 of the singly reflecting TOF MS 91 illustrated in FIG. 9 has a tilted trajectory (illustrated by a dashed-line-portion of the continuous ion beam 96). The tilted trajectory of the continuous ion beam 96 by offsetting the beam trajectory by a small angle α (for example an a between 5-10 degrees) relative to an X-axis of the TOF MS 91. An electrical pulse, applied to the planar buncher 95 adds ion energy only in an X-direction (along the X-axis); thus a change of the ion trajectory angle α occurs that quantitatively depends upon the gained energy. For example, the ion trajectory may become bunched trajectory 97 following the additional energy obtained at the planar buncher 95. The spatial lens 94 is adjusted to focus ions of desired energy onto slit 99. The focusing of the spatial lens 94 provides relatively low resolution energy selection past the planar buncher 95 and admits ions within an approximate 15-20% relative energy spread.

Ion optical simulations of the singly reflecting TOF MS 91 show that the system has a low tolerance for angular spread in the continuous ion beam 96. Nevertheless, though, for typical ion beams (which measure around a few millimeters in size, one degree of angular divergence, and an energy spread of 1 eV), approximately a 5-10 ns width of ion packets may be obtained for 1000 amu ions.

Ion Sources with Wide Spatial Emittance

Referring back to Table 2, the method 31 of axial bunching may be particularly useful applied to ion sources intrinsically having a relatively large emittance compared to the acceptance of the orthogonal accelerator (OA), which estimates:

a=2 mm*deg at K=50 eV, or

A=0.05 mm$^2$rad$^2$eV.

In multiple sources, the problem of emittance matching has been solved by using dampening RF-only ion guides (RFG) to confine the size of the ion beams between 0.3-1 mm at a thermal energy of 0.026 eV. That is, to calculate full emittance:

RFG emittance $E$=0.003-0.03 mm$^{2}$*eV     (Equation 6)

In such cases, the OA acceptance is no longer a limitation, and the OA scheme is preferred (at least for singly reflecting TOF) since it provides for a better duty cycle (as discussed previously). However, use of RFG may prove to be undesirable due to certain practical considerations. Examples of such considerations may include: (a) slowing down the ion transfer at rapid profiling or separations; (b) additional ion molecular reactions in the RFQ; (c) an emittance that depends on ion currents above 1-10 nA, which causes additional losses between the RFQ and the OA; (d) additional gas loads onto a surrounding analyzer or ion source; (e) limited acceptance of the RFQ, which may exceed the source emittance; (f) limited mass range of the RFQ (i.e. an inability to transfer light ions) and poor confinement of heavy ions; and (g) additional cost of the RFG. In situations where these considerations are weighed heavily, the axial bunching method 31 of this disclosure may be preferred.

Figure 12:
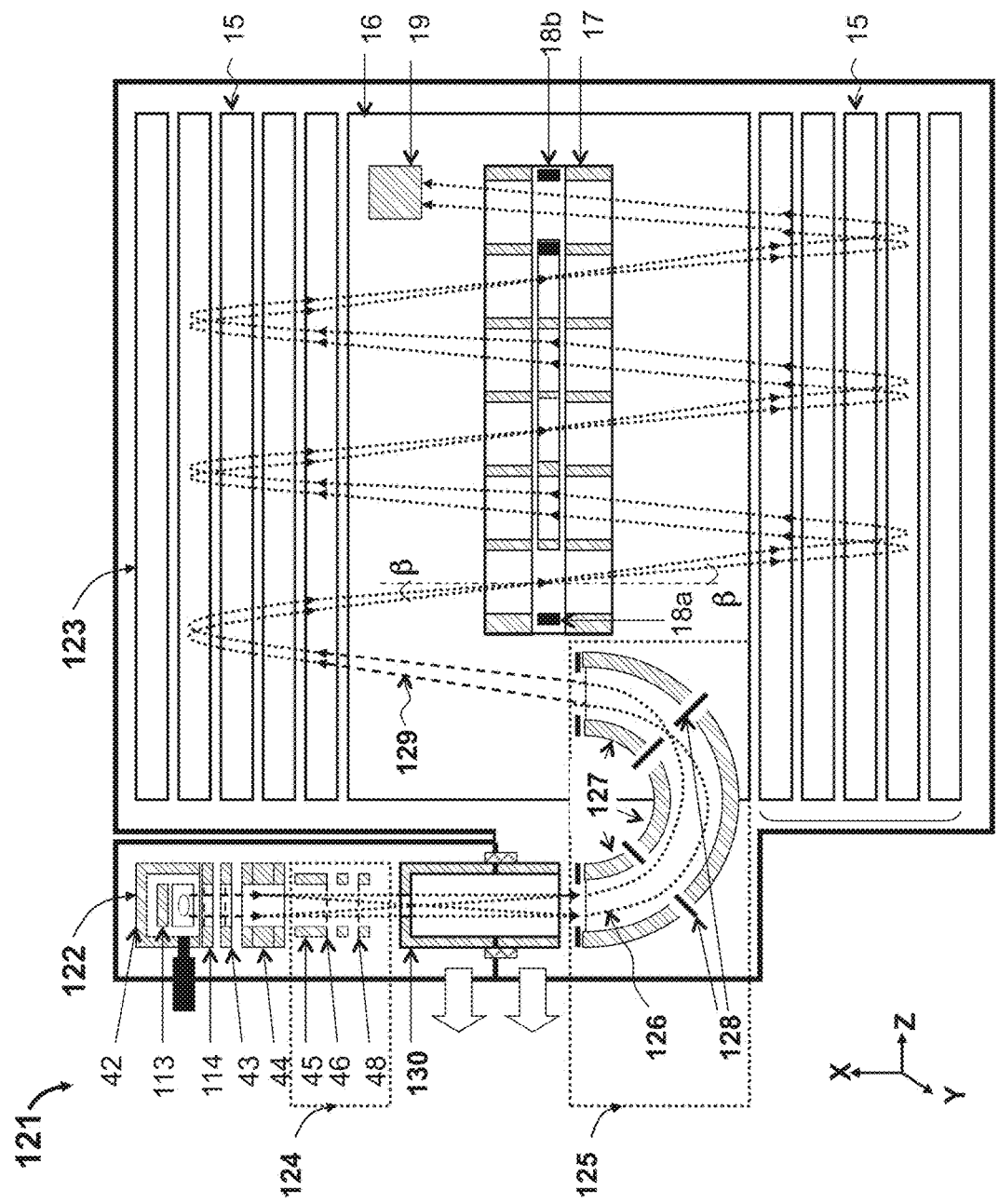
FIG. 12 presents a schematic view for multi-reflecting TOF MS coupled to axial buncher and energy filter.

Referring back to FIG. 4 and also jumping to FIG. 12, the ion sources 42 (or 122) may comprise either a CI, a closed EI, or a semi-open EI source as described in WO2013163530, which is incorporated herein by reference. The emittance level of those sources approximates 10 mm$^2$rad$^2$eV, which is close to the acceptance of MR-TOF analyzers but far exceeds the acceptance of the OA. In such cases, axial bunching provides a substantial gain in the pulse conversion efficiency.

The ion source 42 may be embodied as a source with a larger associated emittance and a larger associated energy spread. For example, a glow discharge ion source at 0.1-1 Tor gas pressure or ICP sources may be utilized. Yet another ion source 42 embodiment is a SIMS or MALDI source wherein the primary beam raster across the surface and where the energy filter and mass analyzer provide spatial imaging in addition to a time-of-flight focusing.

The disclosed method of axial bunching is suitable for very wide ion beams (for example, up to a 3 mm-10 mm range without affecting pulse width by energy filtering time aberrations and up to 100 mm or higher at some comprised energy filtering or time spread.

Bunching Past Gaseous Ion Guides

Figure 10:
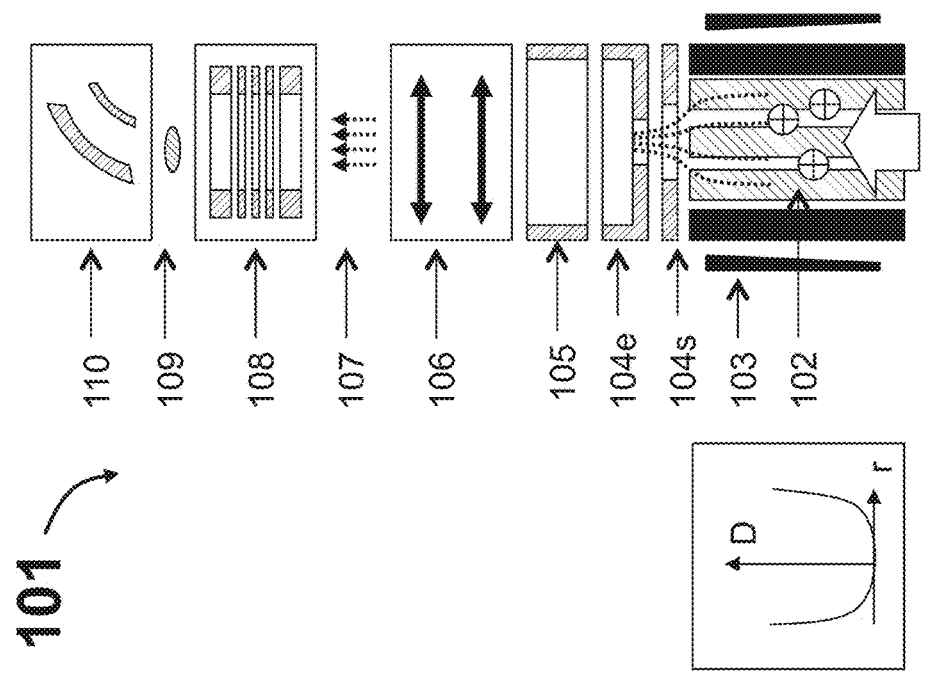
FIG. 10 presents a schematic view for coupling of radio frequency ion guides with axial buncher.

Referring to FIG. 10, an implementation of a pulsed converter 101 includes a gaseous radio-frequency (RF) ion guide 102, an axial DC field 103, a shield electrode 104s, an extraction electrode 104e, a DC acceleration stage 105, a spatially focusing lens system 106, a pulsed buncher 108, and an energy filter 110. The gaseous RF ion guide 102 is a wide bore ion guide (i.e. having a bore width of at least 6 mm-more preferably between 10 mm and 15 mm) having a shallow dynamic well radial distribution D(r), as depicted at the icon of FIG. 10. The shallow D(r) well is to be formed either within high order multipoles (i.e. 8-poles, 10-apoles, or 12-poles) or within an ion tunnel that is formed by rings with alternated RF phases. The ion guide 102 is filled with gas having a pressure range of 1-100 mTor for collisional ion dampening. Preferably, the gaseous RF ion guide 102 includes the axial DC field 103, which may be embodied as: wedge auxiliary electrodes; tilted RF rods with variable penetration of the DC field; resistive RF rods; resistive auxiliary electrodes; segmented rods; auxiliary electrodes; or the like.

In operation, the high multipole ion guide 102 provides collisional dampening of the incoming ion beam and forms a shallow potential well D(r), which can adopt large ionic currents without exciting ions to high energies at the central part of multipoles. Ion motion through the multipole ion guide 102 is preferably assisted by a soft axial DC gradient of a few Volts to reduce space charge effects on ion energy distribution. A combination of shield electrode 104s and extraction electrode 104e enables moderate spatial ion focusing beyond the multipoles of the ion trajectory. That moderate spatial ion focusing is illustrated in FIG. 10 by dashed lines showing ion trajectory.

The extraction is arranged to minimize ion energy distortion. A small extracting DC gradient (i.e. of a few Volts) allows adiabatic ion motion. Notably, ions would not gain additional energy in fringing RF fields. Sampling ions of a core region only (even accepting ionic losses at ion extraction) also reduces effects of RF field onto ion energy. Such a system is capable of forming a continuous ion beam having an ion energy spread well under 1 eV, while providing lower spatial confinement compared to conventional RF-only quadrupoles.

In the DC acceleration stage 105 of the pulsed converter 101, which is beyond the region of gas collision, the continuously and softly extracted ion beam is DC accelerated to an energy range in the keV. The spatially focusing lens system 106, which may optionally be embodied as a telescopic lens system, forms a substantially parallel ion beam 107. This focusing enables the beam to expand spatially for the sake of low angular divergence. The pulsed buncher 108 pulse-accelerates the beam and forms ion packets 109, while the energy filter 110 cuts off a portion of the ion packets 109 that have an excessive energy spread. The system 101 prepares ion packets 109, which are then preferably DC accelerated and analyzed in a TOF MS with wide energy acceptance (not shown in FIG. 10). Such a system 101 is capable of forming sub-nanosecond ion packets and providing a duty cycle ranging between 20-30%. Thus, bunching of pulsed ion packets provides an additional enhancement of the duty cycle of the converter.

Bunching of Soft Pulsed Packets

Figure 11:
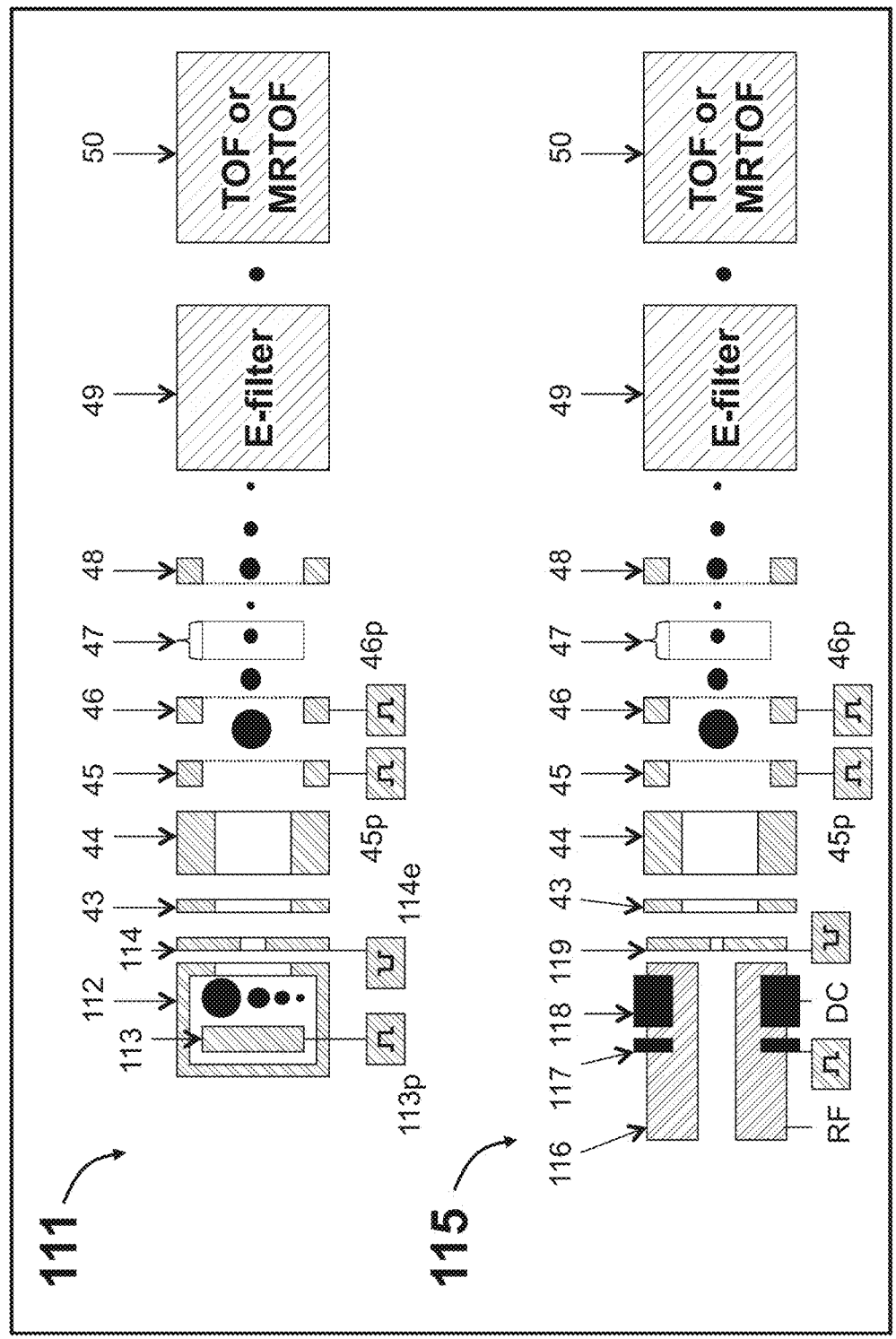
FIG. 11 presents a schematic view for buncher embodiment past soft pulsing ion sources.

Referring to FIG. 11, another embodiment 111 of the axial bunching apparatus of the disclosure includes the following sequentially and axially aligned components: an accumulating ion source (illustrated as an ion chamber 112, a repeller 113, and an extractor 114); a continuous acceleration stage 43; a spatially focusing lens 44; a time selector 45; a buncher 47 formed with parallel electrodes 46, 48; an energy filter 49; and a TOF analyzer 50, which may be either a Re-TOF MS or a MR-TOF MS. Pulse generators 45p and 46p are connected, respectively, to the time selector 45 and the electrode 46. Accordingly, the time selector 45 is optionally embodied as an additional electrode.

The accumulating ion source chamber 112 of the embodiment 111 of FIG. 11 includes at least one electrode 113 for soft pulse extraction of ion packets having: $\Delta T \approx 1$ μs; and a small energy spread of about $\Delta K \approx 1$ eV. Accordingly the product $\Delta K * \Delta T$ approaches 1 eV*μs. The embodiment 111 includes an exemplary closed electron impact (EI) ion source, which has an ion chamber 112, a repeller 113 connected to pulse generator 113p, and an extractor 114 connected to a pulse generator 114e. An analyzed sample is supplied via, for example, a gas chromatograph with typical 1 mL/min flow of carrier gas (typically Helium or Hydrogen). Gas pressure in the ion source may be maintained at between 0.5 and 10 mTor depending on the source opening, which has a diameter that may vary between 1 mm and 4 mm. An electron beam of 0.03-3 mA current at 70 eV ionizes the sample. Periodically, a small amplitude pulse (i.e. a pulse having an amplitude of a few Volts) is applied to repeller 113. Pulse generator 114e applies tens of volts to extractor 114 for soft extraction, which forms ion packets having a duration between 1-2 μs and an energy spread between 1-2 eV, as described in WO2012024468, which is incorporated herein by reference.

In operation, the ion source generates ion beams from ions of a wide mass range as presented by the black circles of different sizes within the ion chamber 112. The continuous acceleration stage 43 continuously accelerates the ion beams to a mean energy $K_C$, which is selected to be at least ten times larger than the energy range $\Delta K$ (100-3000 eV). The absolute velocity spread of ion beam drops as described by (Equation 3). Spatially focusing lens 44 spatially focuses the ion beam onto the energy filter 49. Low relative energy spread is helpful to avoid chromatic lens aberrations. The spatially focusing lens 44 may be incorporated into (or share some of electrodes with) the ion source, the accelerator 43, or the time selector 45.

Each of the pulsed packets may enter the buncher 47 (formed by electrodes 46 and 48) at a different time depending on ion mass of the packets. A bunching pulse is applied to at least one electrode (in embodiment 111, the bunching pulse is applied to electrode 46 via pulsed generator 46p) at a preselected time for bunching of a relatively narrow mass range. Ions of other masses will gain a different amount of energy than the ions of the relatively narrow mass range and will be filtered out by the energy filter 49. Thus, the scheme generates ion packets within a limited mass range, however with a significantly higher duty cycle compared to the bunching of a continuous ion beam in the embodiment illustrated in FIG. 4. These properties associated with embodiment 111 may be useful during parent mass selection or target analysis, wherein a mass of an analyzed compound (in GC-MS, related to chromatographic time) is known before the analysis.

In order to increase the dynamic range of the pulsed ejection scheme of the embodiment 111, preferably, the bunching pulse is applied frequently (much faster than time period required for heaviest ions to pass the MR-TOF analyzer) and with encoded pulse intervals (EFP) as described in WO2011135477, which is incorporated herein by reference. Such fast pulsing is likely to reduce space-charge saturation in the ion source chamber 112 and is also likely to produce reductions as required due to the dynamic range of a detector and of a data system in the TOF analyzer 50.

Specifically regarding the efficiency of the "double" pulsed scheme of embodiment 111 utilizing a closed EI sources (having an opening less than 0.1 cm²), the size of the stored ion cloud is assumed to match the width of the electron beam (i.e. approximately 1 mm thickness). And the ion thermal energy within the closed EI source at the ion accumulation stage is assumed to be 0.5 eV. For soft ejection, the extracting field strength (in the electron beam region) is set at 1 V/mm. The extracted packet is expected to have an energy spread of 1 eV and a turnaround time of 3 μs (for 1000 amu ions). Then the product of time and energy spreads in soft ion packets can be estimated as $\Delta T * \Delta K = 3$ μs*eV. A properly arranged bunching (pulsed acceleration) should preserve this product, which means that, in the TOF focusing plane, the time spread can be reduced to 5 ns corresponding to an increased energy spread of 500 eV at the bunching step to reach nearly a unity duty cycle.

Again referring to FIG. 11, another embodiment 115 of axial bunching apparatus of the disclosure includes the following sequentially and axially aligned components: an accumulating ion guide formed by RF fed multipole rods 116; an auxiliary push electrode 117; an auxiliary DC trap electrode 118; an exit skimmer 119; a continuous acceleration stage 43; a spatially focusing lens 44; a time selector 45; a buncher 47 formed with parallel electrodes 46, 48; an energy filter 49; and a TOF analyzer 50, which may be embodied as either an Re-TOF MS or MR-TOF MS. Pulse generators 45p and 46p are connected, respectively to the time selector 45 and the 46. Accordingly, the time selector 45 is optionally embodied as an additional electrode. Another set of pulse generators is connected to the auxiliary push electrode 117 and the exit skimmer 119.

In operation, an incoming ion beam, preferably promoted by a DC axial field within a multipole guide, gets stored with an axial DC well formed by DC potentials from the auxiliary push electrode 117, the auxiliary DC trap electrode 118, and the exit skimmer 119. During this ion beam storage, the ion beam remains radially confined by the RF field of multipole rods 116. Periodically soft extraction pulses (for example, pulses at a few Volts to a few tens of Volts amplitude depending on the efficiency of penetration of auxiliary fields) are applied to the auxiliary push electrode 117 and the exit skimmer 119. Optionally, the RF field on rods 116 may be turned off a few microseconds prior to the extraction pulses. The soft extraction field is adjusted to about between 0.3 and 1.0 V/mm. Soft extraction may introduce a very minor energy spread (i.e. under 1 eV) while forming sub-microsecond ion packets. The scheme 115 is expected to provide for unity duty cycle at the bunching stage for a limited mass range, while generating sub-nanosecond ion packets for TOF MS analysis.

Example of MR-TOF MS with Axial Bunching

Referring to FIG. 12, an embodiment 121 of the multi-reflecting time-of-flight mass spectrometer (MR-TOF MS) with axial bunching of this disclosure includes a continuous ion source 122, followed by axial buncher 124, coupled to a MR-TOF analyzer 123 via an isochronous curved inlet (C-inlet) 125. The C-inlet 125 is designed for ion trajectory steering at an angle defined as 180-β—where β is the tilt angle of ion trajectories 129 in the MR-TOF analyzer 123. The ion source 122 and the axial buncher 124 are similar to those of FIG. 4 for an MR-TOF analyzer 123 that is similar to that of FIG. 1. A particular shown variant of C-inlet 125 comprises three sets of electrostatic sectors 127 separated by apertures 128, wherein either of the apertures 128 is placed in the plane of spatial and angular focusing to serve as an energy filter.

MR-TOF analyzer 123 includes a pair of parallel gridless ion mirrors 15, separated by a drift space 16, a periodic lens 17 with optional steering plates 18a, 18b, and a detector 19.

Preferably the drift space 16 is floated at an acceleration potential in order to keep the source 122 at a ground. The analyzer 123 is designed to arrange the jigsaw ion trajectories 129, thus folding an extended flight path within a moderate-sized analyzer. The MR-TOF analyzer 123 may be either planar as shown in FIG. 12 or cylindrical as described in WO2011107836, which is incorporated herein by reference, for extending the number of reflections within a compact analyzer. The analyzer may comprise ion mirrors 15 having a third order energy focusing as described in WO2005001878 or of higher order focusing as described in WO2013063587, both of which are incorporated herein by reference.

In operation, a continuous ion beam formed in the source 122 with soft extraction to minimize ion energy spread, is accelerated to an energy range of keV in an DC acceleration stage 43, shaped by a spatially focusing lens 44 for minimal angular divergence and spatial focus at an energy filtering slit 128. An axial buncher, which is formed by an entrance section 46 and an exit section 48, modulates the beam to form ion packets with excessive energy spread. The ion packets pass the differential pumped tube 130 (used to maintain high vacuum within the analyzer 123) and enter the C-inlet 125, which has been further illustrated in FIG. 7 and described above. Three electrostatic sectors 127 are terminated by the slits 128, wherein one of the slits 128 serves as a crude energy filter by passing only an ion beam with a 5-7% relative energy spread. The C-inlet 125 is designed to emit ion packets at and angle defined as 180°-β while forming the ion packet time-fronts parallel with the ion mirrors 15. The C-inlet 125 may be used for fine adjustment of the position and angle of the ion packets at the MR-TOF entrance by introducing a voltage adjustment on so-called Matsuda plates (not shown), which work as cap electrodes around an electrostatic sectors. Such adjustment is allows an independent adjustment of the of the time-front inclination, as described in WO2006102430, which is incorporated herein by reference. Ion packets follow the jigsaw ion trajectory 129 towards the detector 19, while being spatially confined by the periodic lens 17 in a Z-direction arranged along a Z-axis and by the gridless ion mirrors 15 in an X-direction along a Z-axis.

In order to increase the duty cycle of the pulsed conversion, the bunching pulse of the buncher 47 is applied frequently (much faster than required for heaviest ions to pass the MR-TOF analyzer) and with encoded pulse intervals (EFP) as described in WO2011135477, which is incorporated herein by reference. As a numerical example, the average period of bunching pulses may be 10 µs, and the effective time of the buncher may be 1 µs at 1-2 ns packet FWHM, which corresponds to a 10% time duty cycle of the pulsed conversion.

Space Charge Limitations and Pulsing Schemes

High intensive ion sources—such as a closed EI source, glow discharge, or an ICP source—generate ion currents in excess of 10 nA range (1E+11 ions/sec) and are very likely to cause space charge limitations in the analyzer. At $T_{EFF}=1$ µs, the number of ions per packet may reach 1E+5 ions/shot for ions of a wide m/z range. The MR-TOF analyzer is known to sustain resolution for ion packets up to 300-1000 ions and to maintain unaffected mass accuracy up to 2-3E+4 ions per packet of one m/z.

Referring back to FIG. 4, the axial bunching scheme enables an adjustment to the number of ions per packet. Ion beam deeming could be achieved at least by the following methods: (a) accelerating a continuous ion beam to higher energies at the same bunching amplitude; (b) applying higher pulse amplitudes at the bunching step, which may be arranged with symmetric push and pull pulses to electrodes 46 and 48 to avoid distortion of the average energy; (c) spatial defocusing of ion packets in the lens 44 past an ion source 42; (c) using time-selector 45 for partial trimming of extracted ion packets to fit the acceptance of the energy filter 49. When dealing with intense ion sources, the scheme is initially adjusted for a low duty cycle (high energy of the continuous ion beam and high pulse amplitude for reducing effective time $T_{EFF}$ under 0.1 µs), while dynamic range and sensitivity are recovered by the method of encoded frequent pulsing at an average pulsing frequency up to 100 kHz. The method allows for the reduction of turnaround time to under ins and for the improvement of MR-TOF resolution. At 1E+11 ion/sec flux past the source, and at $T_{EFF}=0.1$ μs, the number of ions per shot drops to 1E+4 (thus avoiding space charge effects in MR-TOF), while overall flux onto the TOF detector 19 becomes 1E+9 ions/sec.

Figure 13:
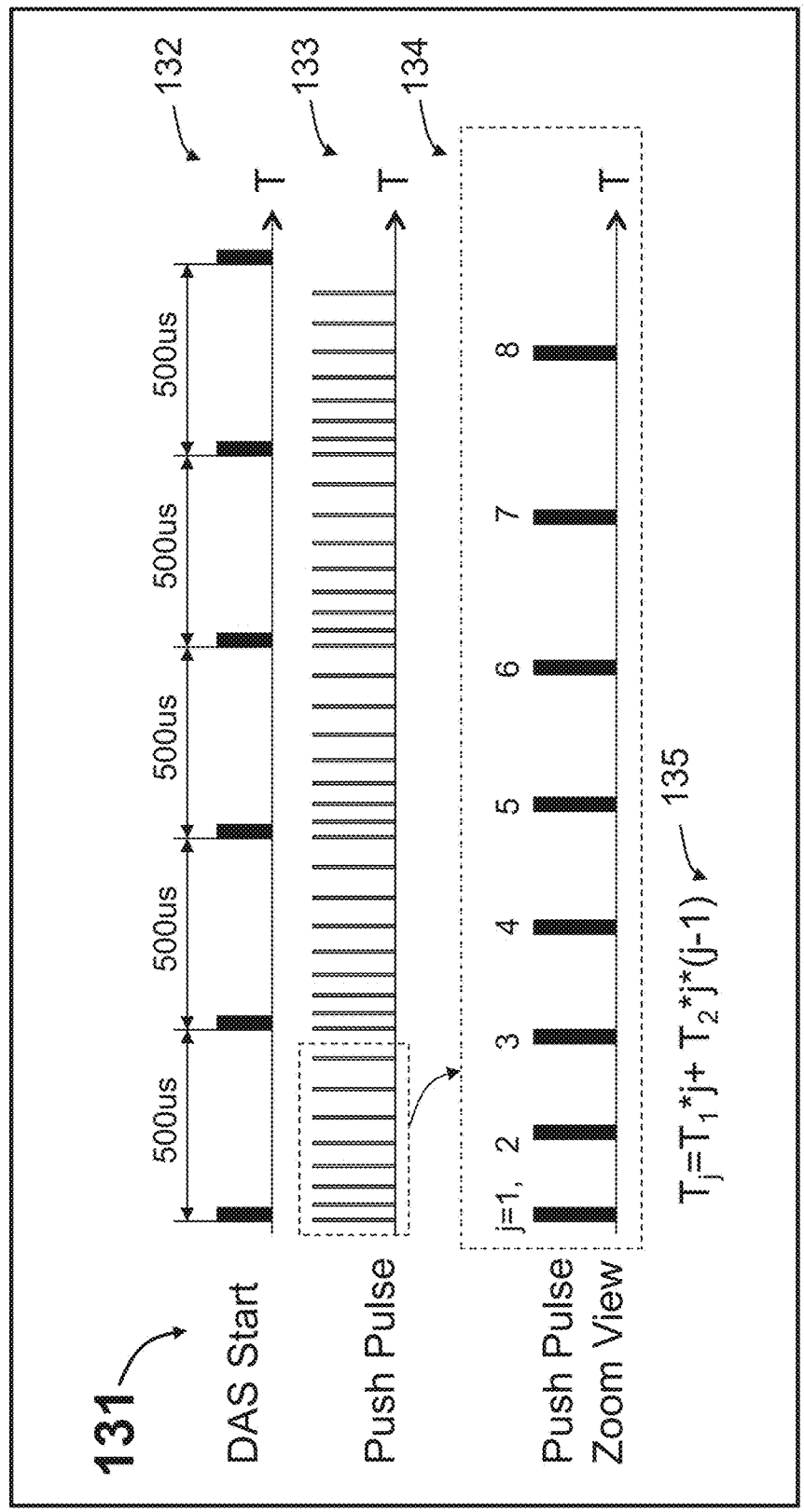
FIG. 13 shows time diagram for method of encoded frequent pulsing of prior art being applied to bunching method of the present invention.

Referring to FIG. 13, a time diagram 131 to plotted to describe details of the frequent encoded pulsing method. A DAS Start graph 132 of the time diagram 131 depicts periodic pulses, triggering a data acquisition system (DAS). The plotted period is shown as an exemplary period of 500 μs, which corresponds to the longest ion flight time in the exemplar MR-TOF analyzer. A Push Pulse graph 133 of the time diagram 131 depicts bunching pulses applied in strings over the 500 μs duration. Details of a single 500 μs pulse string are more clearly seen in a zoom view 134 of the time diagram 131. An exemplary string with unique time intervals is described by formula 135: $T_j=T_1*j+T_2*j*(j-1)$, where j is the pulse number in the particular string, $T_1$ is an average period between pulses (typically 10 μs), and $T_2$ represents a chosen time increment that is wider than the peak width (for example, $T_2=20$ ns). Additional details regarding spectral encoding and decoding are provided in WO2011135477, which is incorporated herein by reference. In high resolution MR-TOF, a mass spectra may be sparse enough to increase the spectral population by 30-50-fold. If necessary, the spectral population may be reduced by a partial mass filtering (for example, by suppressor/time selection gate 45 illustrated in FIG. 4 and described previously or by pulsed extraction out of the source as illustrated in FIG. 11 and described previously) to maximize the duty cycle at some moderate mass range for the target analysis. For continuous ion source currents as high as 10 nA and an axial bunch converter overall duty cycle as high as 10%, the ion flux onto the TOF detector may reach 1E+10 ions/sec. This level of flux requires special TOF detectors with an extended life time and an extended dynamic range, which is further described hereinafter.

Long Life Detector

In order to accommodate ion fluxes up to 1E+10 ions/sec, this disclosure discloses the following novel combination that results in a strong enhancement of dynamic range and life time of the detector.

Figure 14:
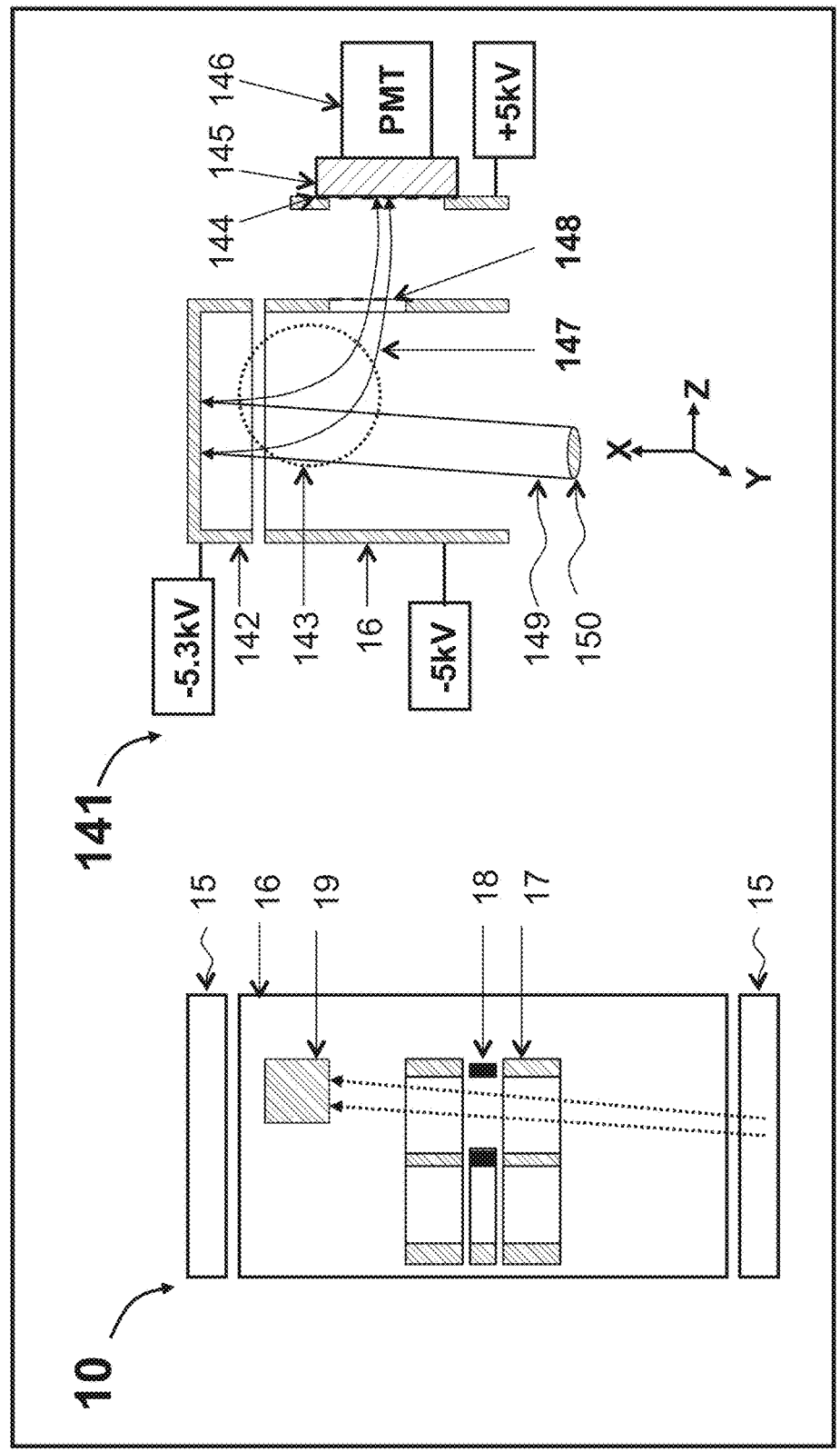
FIG. 14 depicts a schematic view of a long life detector.

Referring to FIG. 14, an embodiment 141 of the improved time-of-flight detector comprises a conductive converter 142, magnets 143, a scintillator 145, that is coated or covered by a conductive mesh 144, and a sealed photomultiplier 146. In a sense, the detector 141 is similar to a wide spread Daly detector, but the detector 141 provides the novel improvement to the time-of-flight performance. FIG. 14 also illustrates a portion of the MR-TOF analyzer 10 that shows the location of the detector 19 (which may be embodied as the improved time-of-flight detector 141) within the MR-TOF analyzer 10.

Referring to the improved time-of-flight detector 141, in operation, the conductive converter 142 is installed parallel to a time front 150 of the impinging ion packets (the time front 150 being illustrated at trajectories 149) in a Y-Z plane, normal to an X-axis of the improved time-of-flight detector 141. The conductive converter 142 is floated negative by several hundred volts relative to a charge of the analyzer drift space 16. For example, in FIG. 14, the potential difference is 300V (referring to −5 kV charge shown for the analyzer drift space 16). Ions hit the converter at 5-6 keV energy (accounting acceleration in the pulsed source), and emit secondary electrons with an ion-to-electron efficiency that approaches unity for small molecules (typically under 500 amu) analyzed in GC-MS. Emitted electrons are accelerated by the 300V difference between analyzer drift space 16 field and the conductive converter 142 field while being steered to steered trajectories 147 by a magnetic field provided by the magnets 143. The magnets 143 are installed to form magnetic lines along a Y-axis, which steers the emitted electrons in a Z-direction. The voltage bias between the conductive converter 142 and the analyzer drift space 16 is adjusted relative to a given strength of the magnetic field (which are optionally chosen between 30 and 300 Gauss) to provide for focusing of electrons onto the scintillator 145. The axis of the magnets 143 is optionally shifted from an ion beam direction. This shift provides an additional electron confinement in the Y-direction (accounting for the curvature of magnetic lines), while 90-degree magnetic steering provides natural electron confinement in an X-direction. Electrons along steered trajectory 147 are sampled through a mesh covered window 148 and accelerate to the positively-biased scintillator 145. Higher scintillator 145 biasing (for example, up to +10 kV) yields a higher signal gain but may be limited for practical reasons. The scintillator 145 is optionally embodied as a fast organic scintillator (BC418 or BC422Q by St. Gobain Ltd.), which supports a high electron-to-photon efficiency (for example, at least 1 photon per every 60-100 eV of electron energy). Thus, a single secondary electron having 10-15 kV of energy forms at least 15 photons. This allows reliable detection of almost every primary ion, in spite of limited efficiency of photon collection (estimated in our experiments as ~20%) and in spite of a limited photon efficiency (25-30%) of a photo-emitter in the PMT 146.

Conventional hybrid TOF detectors employ an additional microchannel (MCP) stage in front of the scintillator 145 in order to enhance the overall signal gain. Also, conventional hybrid TOF detectors employ a thin (approximately 1 μm) aluminum coating on top of the scintillator 145 to prevent scintillator charging and to enhance photon collection. Those two features strongly limit both the life time and dynamic range of the detector. The embodiment 71 of the pulsed converter shown in FIG. 7 addresses those limitations. There is no saturation of MCP (known to occur at 1E+7 ions/sec/cm² flux density), the electron dose onto scintillator 145 is reduced 100-1000 fold (since there is no MCP amplification). Additionally, no thin aluminum coating, which appears to suppress fast electrons at low reproducibly, is utilized. Thus, the embodiment 71 of the pulsed converter of FIG. 7 also avoids damaging such an aluminum coating by large ionic doses. Instead, a deposited or covering thick metal conductive mesh 144 provides electrostatic removal of the electron charge by surface discharges and leaks at 1 kV/mm at an optional exemplary 0.3-1 mm cell size of the conductive mesh 144. Other cell sizes may be utilized.

Hamamatsu (in R9880U, which is incorporated herein by reference) provides additional details regarding commercially available PMT amplifiers 146. Such sealed photomultiplier (PMT) 146 may have an extended life time 300 Coulomb (as measured by the output charge) while providing a relatively short rise time (for example, 1.5 ns). At an overall gain of 1E+6 an average ion flux of 1E+9 ions/sec, the output current is 160 μA. To this end, the detector 141 is expected to survive for 2E+6 seconds (i.e. almost 500 hours at a maximal load and for at least a year at standard loads). For an external PMT coupling (for example, via a glass tube for passing photons) the PMT module 146 could be replaced without venting the instrument. External PMT coupling also suppresses pick-up from pulse generators in a frequent pulsing mode, such as the frequent pulsing illustrated in FIG. 6 and described above.

The linear range of the detector 141 (which is normally limited by the output current to 100 μA by a standard resistive divider) can be improved. For example, the last few stages are fed by a more powerful supply (i.e. at least having a several mA current limit) and being controlled by active circuits. To enhance the dynamic range of the detector 141, the last PMT 146 stages are connected to buffer capacitors. Such a solutions, however, may be insufficient for temporal peak signals. Further enhancement of the dynamic range can be realized by using: (a) frequent encoded pulses in the source, which drops the maximum signal of the detector 141 by two orders of magnitude; or (b) alternated gain pulses, followed by an amplifier with fast cut-off and rapid recovery. Both of these improvements have been further described above and are illustrated in FIG. 6. The dynamic range may be further improved by: (a) using dual PMT 146 each having a different efficiency of light collection; (b) taking signals from different PMT stages 146; (c) using preamplifiers with dual (triple) gain outputs; and/or (d) alternating either electron collection efficiency or PMT gain between shots.

The disclosed so-EI-MR-TOF instrument with highly efficient axial bunching would be quite practically limited if using (a) conventional (rare pulses) operation regime and (b) conventional TOF detectors with short life time (typically 1 Coulomb for standard MCP and non-sealed SEM). The proposed methods of encoded frequent pulsing and proposed long life detector solve those problems to practically enable an axial bunching method 31 for high resolution MR-TOF MS.

Tandem Time-of-Flight Mass Spectrometers

The disclosed axial bunching method 31 is well-suited for generating ion packets with the aim of selecting parent ions in a time-of-flight mass spectrometer (TOF MS).

Figure 15:
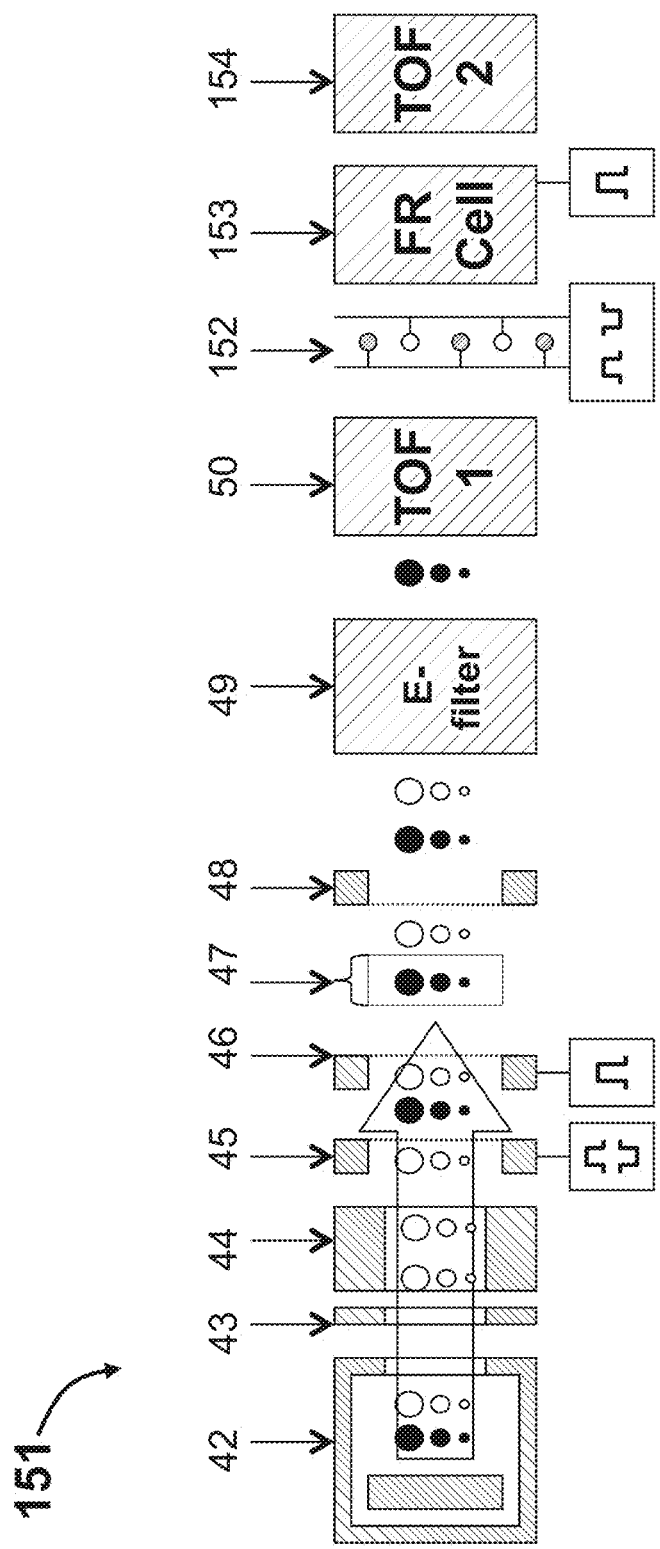
FIG. 15 depicts a schematic view of TOF-TOF with axial bunching of the present invention.

Referring to FIG. 15, the tandem TOF MS 151 (TOF-TOF MS) is disclosed that includes the following sequential components: a continuous source 42; a continuous acceleration stage 43; a spatially focusing lens 44; a suppresser 45, which may be an electrode; a buncher 47 formed in a bunching region 47 between parallel electrodes 46 and 48; an energy filter 49; a first TOF analyzer 50 (TOF1), which may be embodied as either Re-TOF or MRTOF for separating ions in time; a time ion selector 152, which may be embodied as an electrode that selects parent ions of a particular m/z rations of interest; a fragmentation cell 153, which may be embodied as an electrode; and second TOF analyzer 154 (TOF2) for analyzing fragment ions. Pulse generators, depicted in FIG. 15 as gate icons are connected to the suppressor 45, the first parallel electrodes 46, and the time ion selector 152. Additionally, a pulsed generator is shown connected to the fragmentation cell 153. This pulsed generator connected to the fragmentation cell 153 is an optional feature of the TOF-TOF MS 151.

Referring to the TOF-TOF MS 151 of FIG. 15, in operation, pulsed ion packets of parent ions are formed from a continuous ion beam by the method 31 of axial bunching followed by energy filtering as described previously and illustrated in FIG. 4. The first TOF analyzer 50 separates parent ions in time, and time ion selector 152 (which, for example, may include a bipolar mesh to carry out its function) selects parent ions of interest and admits them into the fragmentation cell 153. After fragmentation, ion packets are optionally pulsed and DC accelerated. Then, the fragmented ions are mass analyzed in the second TOF analyzer 154. The fragmentation cell 153 may comprise one of the following: (i) a surface-induced dissociation SID on a surface that is arranged parallel to the time front 150 of the ion packets and facing the primary ion packets; (ii) a surface-induced dissociation SID arranged at a gliding angle relative to trajectory 149 of parent ion packets; (iii) a collisional-induced dissociation CID within a short CID cell with length L under one centimeter at a gas pressure P adjusted for product P*L falls within the range of 1-5 cm*mTor to correspond with a single average collision of parent ions; (iv) a collisional-induced dissociation CID arranged within the source having a source opening area that falls within the range 0.1-0.3 cm$^2$; (v) a pulsed acceleration step occurring after the fragmentation step; (vi) a spatial focusing lens that provides spatial focusing after the fragmentation step; (vii) a post-acceleration step of fragment ion packets occurring after the fragmentation step; or (viii) a steering step that occurs after the fragmentation step. Additional details related to these fragmentation methods, which are all suitable for the TOF-TOF MS 151, are disclosed in US2007029473, WO2013192161, and a co-pending application on semi-open source for MR-TOF MS, each of which is incorporated herein by reference.

Although the present invention has been describing with reference to the preferred embodiments previously described, it will be apparent to those skilled in the art that various modifications in form and detail may be made without departing from the scope of the present invention as set forth in the accompanying claims.

A number of implementations have been described. Nevertheless, it will be understood that various modifications may be made without departing from the spirit and scope of the disclosure. Accordingly, other implementations are within the scope of the following claims.

What is claimed is:

1. A time-of-flight mass spectrometer comprising:
    a continuous or quasi-continuous ion source, generating an ion beam;
    a continuous acceleration stage, accelerating said ion beam to an energy level at least ten times greater than an initial energy spread in said ion beam and reducing an absolute velocity spread of said ion beam;
    a pulsed buncher receiving said accelerated ion beam from said continuous acceleration stage, supplying a bunching pulse, and comprising at least one electrode connected to a pulsed voltage supply for ion acceleration or deceleration substantially along a direction of said ion beam;
    an isochronous energy filter transmitting ions within an energy acceptance range; and
    a singly or multi-reflecting time-of-flight mass analyzer comprising a time-of-flight detector.

2. The spectrometer of claim 1, further comprising a suppressor for rejecting ions approaching said pulsed buncher, said rejected ions having energies responsive to said bunching pulse, said suppressor comprising at least one electrode connected to a pulse generator.

3. The spectrometer of claim 1, further comprising:
    a spatially focusing lens in front of said pulsed buncher for a purpose selected from the group consisting of: (i) reducing an angular spread of said ion beam, so that an axial energy spread within said pulsed buncher remains comparable to an initial energy spread past said ion source; (ii) spatial focusing of ion packets onto a slit or an aperture of said isochronous energy filter; and (iii) a combination thereof.

4. The spectrometer of claim 1, further comprising:
a data acquisition system that triggers said pulsed buncher and records a waveform signal from said time-of-flight detector, said data acquisition system comprising a spectral analysis system.

5. The spectrometer of claim 4, wherein said pulsed buncher further comprises a pulse generator with average frequency of at least 50 KHz, wherein said data acquisition system comprises a triggering clock capable of forming a preset string of pulses with mostly unique time intervals between pulses; and wherein said data acquisition system comprises means for decoding partially overlapping spectra based on said mostly unique pulse intervals.

6. The spectrometer of claim 1, wherein said energy filter comprises an aperture or a slit at a plane of ion packet spatial/angular focusing for central ion energy and one chromatic ion optical element selected from the group consisting of: (i) at least one isochronous electrostatic sector; (ii) at least one spatially focusing and isochronous gridless ion mirror; (iii) at least one pair of deflectors; (v) a set of periodic lens; (vi) at least one chromatic lens; and (vii) a combination of the above elements.

7. The spectrometer of claim 1, further comprising:
a dual or single stage chromatograph sequentially prior to said ion source, wherein said ion source is selected from the group consisting of: (i) closed electron impact ion source; (ii) semi-open electron impact ion source with total opening area within a range of 0.1-1 cm2 and positively-biased electron slits; (iii) chemical ionization source; (iv) chemical ionization source upstream of an electron impact ion source; (v) photochemical ionization source; (iv) conditioned glow discharge ion source; (vi) cold electron impact ion source with analyte internal energy cooling in supersonic gas jet; and (vii) field ionization source.

8. The spectrometer of claim 1, further comprising:
a gas-filled RF-only ion guide between said ion source and said continuous accelerator, wherein said ion source is selected from the group consisting of: (i) an ESI ion source; (ii) an APCI ion source; (iii) an APPI ion source; (iv) a gas filled MALDI ion source; (v) an EI ion source; (vi) a CI ion source; (vii) a cold EI ion source; (viii) a photo-chemical ionization ion source; and (ix) a conditioned glow discharge ion source.

9. The spectrometer of claim 8, wherein said ion source or said gas-filled RF-only ion guide is configured to accumulate ions and to pulse eject ion packets at an energy spread under 10 eV.

10. The spectrometer of claim 1, wherein said time-of-flight detector comprises:
a conductive plate for converting impinging ion packets into secondary electrons;
at least one magnet for diverting trajectories of said secondary electrons by an angle between 30 degrees and 180 degrees;
a scintillator coated or covered by a conductive mesh; and
a sealed photo-electron multiplier sequentially following said scintillator,
wherein said converter plate has a potential that is floated negative relative to a potential of a drift region of the spectrometer; wherein said converter plate is aligned parallel to a time front of detected ion packets, and wherein a potential of said conductive mesh is adjusted to a value at least +1 kV more than said potential of said converter plate.

11. A method time-of-flight mass spectrometric analysis sequentially comprising:
ionizing ions in an ion source and generating a continuous or quasi-continuous ion beam with an initial energy spread under 10 eV;
continuously accelerating said ion beam to an energy level having an average of at least 10 times larger than said initial energy spread and reducing an absolute velocity spread of said ion beam;
spatially focusing said ion beam at a plane of spatial focusing while maintaining ion angular spread within a limit so that axial ion energy spread remains comparable to said initial energy spread;
bunching said accelerated ion beam with a pulsed accelerating or decelerating electric field constrained by time and space within a bunching region, thus forming ion packets;
isochronously filtering energy of said ion packets by chromatically deflecting or focusing said ion packets and removing ions with unwanted energies on at least one aperture, located in said plane of spatial focusing, while passing through ions, fitting within an energy acceptance range of a subsequent time-of-flight mass analysis step;
separating ion packets in time at isochronous single or multiple reflections in an electrostatic field of at least one ion mirror;
detecting said ion packets with a time-of-flight detector to form waveform signal; and
analyzing said waveform signal to extract mass spectral information.

12. A method as in claim 11, further comprising a step of rejecting ions with an energy level from said bunching failing to comply with an energy acceptance range of said time-of-flight detector.

13. A method as in claim 11, wherein said step of isochronous energy filtering comprises:
a step of ion packet skimming by an aperture or a slit; and
a step of isochronous and chromatic ion beam focusing or deflection by one electrostatic field selected from the group consisting of: (i) a deflecting field of an electrostatic sector; (ii) an angled reflecting field of a gridless ion mirror; (iii) a deflecting field of at least one pair of deflectors; (v) a periodic spatial focusing field of a periodic lens; (vi) a focusing field of at least one chromatic lens; and (vii) a combination of the above fields.

14. A method as in claim 11, wherein to increase dynamic range of the method, said step of pulsed bunching has a time period at least 10 times smaller than ion flight time at said time separation step, and wherein the method further comprises:
a step of encoding said bunching pulses with mostly unique time intervals between adjacent pulses at time increments no less than ion packet time width at said detection step; and
a step of decoding partially overlapped signals corresponding to multiple bunching pulses at said spectral analysis step.

15. A method as in claim 11, further comprising:
a step of dual or single stage chromatographic separation prior to said ionization step, wherein said ionization step comprises a method selected from the group consisting of:
(i) ionizing by electron beam within a volume having an opening area less than 0.1 cm$^2$;
(ii) ionizing by electron beam within a volume having an opening area within the range of 0.1-1 cm$^2$ and removing secondary electrons by positively biasing an electrode in a vicinity of said ionizing electron beam;
(iii) chemical ionization;
(iv) an alternation between electron impact ionization and chemical ionization upstream of said electron impact ionization;
(v) photochemical ionization;
(vi) conditioned glow discharge ionization;
(vii) electron impact ionization accompanied by an analyte internal molecular cooling in a supersonic gas jet (cold EI ionization); and
(viii) field ionization.

16. A method as in claim 11, further comprising:
confining said ion beam in gas collisions within a radial non-uniform RF field of an RF ion guide between said ionization and said continuous acceleration steps,
wherein said ionization step comprises a method selected from a group consisting of: (i) ESI ionization; (ii) APCI ionization; (iii) APPI ionization; (iv) MALDI ionization at a fore-vacuum gas pressure; (v) EI ionization; (vi) CI ionization; (vii) cold EI ionization; (viii) photochemical ionization; and (ix) conditioned glow discharge ionization.

17. A method as in claim 16, further comprising:
an ion manipulation step between said ionization step and said gaseous ion confining step,
wherein said ion manipulation is selected from the group consisting of: (i) a mass separation in quadrupolar RF and DC fields; (ii) a time-of-flight mass separation; (iii) a trapping of ions in array of RF and DC field traps followed by a sequential mass dependent ion ejection out of said array of trapping fields; (iv) an ion mobility separation; (v) fragmenting ions; and (vi) a combination thereof.

18. A method as in claim 16, further comprising a step of ion accumulation and pulsed ejection of ion packets at said ionization step or said step of ion confinement in gaseous RF ion guide.

19. A method as in claim 11, wherein to improve a dynamic range of the method, said ion packet detection step sequentially comprises:
aligning a conductive plate parallel to a time front of said detected ion packets;
arranging an accelerating field near a surface of said conductive plate;
converting impinging ion packets into secondary electrons;
steering said secondary electrons to angle between 30 degrees and 180 degrees within a magnetic field from 30 Gauss to 300 Gauss;
accelerating said secondary electrons by at least 1 kV along steered trajectory;
directing said secondary electrons onto a scintillator thus producing photons;
drawing an electrostatic charge from a surface of said scintillator by surface electric leak or discharge towards a conductive mesh that is either covering or coating a surface of said scintillator; and
detecting said photons by a sealed photo-electron multiplier, placed past said scintillator.

20. A method as in claim 11, wherein, to add MS-MS capabilities past said time separation step in electrostatic fields of a time-of-flight analyzer, the method further comprises:
a step of timed ion selection and a step of ion fragmentation selected from the group consisting of:
(i) a surface induced dissociation SID on a surface arranged parallel to time-front and facing primary ion packets;
(ii) a surface induced dissociation SID arranged at a gliding angle relative to a trajectory of parent ion packets;
(iii) a collisional induced dissociation CID within a short CID cell with a length L under 1 cm at a gas pressure P adjusted to maintain product P*L between 1 and 5 cm*mTor;
(iv) a collisional induced dissociation CID arranged within said ion source by choosing an opening area of the source between 0.1 and 0.3 $cm^2$;
(v) a pulsed acceleration past a fragmentation step;
(vi) a spatial focusing by a lens past a fragmentation step;
(vii) a post-acceleration of fragment ion packets past a fragmentation step; and
(viii) a steering past a fragmentation step.

21. A method as in claim 20, further comprising a spectral decoding step comprising correlating a time variation of an ion signal with a chromatographic separation, a ion mobility separation, or a mass separation.

22. A method as in claim 11, wherein to adjust a duty cycle and a time width of said ion packets, the method further comprises:
a step selected from the group consisting of: (i) adjusting a mean energy level of said continuous ion beam at said continuous acceleration step; (ii) adjusting field strength at said bunching step; and (iii) adjusting a transmitted energy spread at a step of energy filtering.

23. A method as in claim 11, wherein said continuous ion beam enters at a small angle between 5 degrees and 20 degrees, relative to a direction of a pulsed accelerating field of a bunching region, and wherein said steps of energy filtering and time-of-flight separation both occur within a singly reflecting ion mirror.

24. A method of pulsed conversion of continuous or quasi-continuous ion beams into ion packets, sequentially comprising:
ionizing ions in an ion source and generating a continuous or quasi-continuous ion beam with initial energy spread under 10 eV;
continuously accelerating said ion beam to a mean energy being at least 10 times larger than said initial energy spread and reducing an absolute velocity spread of said ion beam;
spatially focusing said ion beam at a plane of spatial focusing while maintaining ion angular spread within a limit so that axial ion energy spread remains comparable to said initial energy spread;
bunching said accelerated ion beam with a pulsed accelerating or decelerating electric field constrained by time and space of a bunching region, thus forming ion packets; and
isochronously filtering energy of said ion packets by chromatic deflecting or focusing of said ion packets and removing ions with unwanted energies on at least one aperture, located in said plane of spatial focusing, while passing through ions, fitting a desired energy acceptance.

25. A method as in claim 24, further comprising a step of rejecting ions whose energies from said bunching fail to comply with an energy acceptance range of a subsequent time-of-flight analyzer.

26. A method as in claim 24, wherein said step of isochronous energy filtering comprises:
a step of ion packet skimming by an aperture or a slit; and
a step of isochronous and chromatic ion beam focusing or deflection by one electrostatic field selected from the group consisting of: (i) a deflecting field of an electrostatic sector; (ii) an angled reflecting field of a gridless ion mirror; (iii) a deflecting field of at least one pair of deflectors; (v) a periodic spatial focusing field of periodic lens; (vi) focusing filed of at least one chromatic lens; and (vii) a combination of the above fields.

27. A method as in claim 24, wherein to increase conversion efficiency, said step of ion pulsed bunching is arranged at pulsing periods between 10 μs and 100p; and further comprises a step of encoding said bunching pulses with mostly unique time intervals for subsequent decoding of partially overlapped packets of ions with different m/z.

28. A method as in claim 11, wherein a diameter of said continuous or quasi-continuous ion beam is one of the group: (i) under 1 mm; (ii) between 1 and 3 mm; (iii) between 3 and 10 mm; (iv) between 10 and 30 mm; (v) between 30 and 100 mm; (vi) above 100 mm.

29. A method as in claim 11, wherein time width of said ion packets after said step of energy filtering is one of the group: (i) under 0.1 ns; (ii) from 0.1 to 0.3 ns; (iii) from 0.3 to 1 ns; (iv) from 1 to 3 ns; and (v) from 3 to 10 ns.

30. A method as in claim 24, wherein the bunching step is accomplished grid-free electrodes.

31. A method as in claim 30, wherein the grid-free electrodes are embodied as a set of ring electrodes with uniform distribution of a pulsed accelerating field.

32. A time-of-flight mass analyzer, comprising:
a continuous or quasi-continuous ion source;
an acceleration stage arranged to accept an ion beam emitted by the ion source and to reduce an absolute velocity spread of said ion beam;
a buncher arranged to accept an accelerated ion beam from the acceleration stage;
an energy filter accepting ions from the buncher and isochronously removing a portion of the ions;
a time-of-flight mass separator arranged to accept ions that pass through the energy filter and time-separate the accepted ions; and
a time-of-flight detector residing within or at an end of the time-of-flight mass separator,
wherein the buncher forms ion packets, wherein the time-of-flight mass separator has an associated energy acceptance level, and wherein the energy filter removes ions outside of the energy acceptance level of the mass separator.

33. The analyzer of claim 32, wherein the buncher, which is formed between a first electrode and a second electrode, has a capacitive and resistive divider to generate a nearly uniform pulsed electric field between two parallel electrodes.

34. The analyzer of claim 32, further comprising a spatially-focusing lens arranged to accept the ion beam after the acceleration stage, wherein the spatially-focusing lens is constructed to focus a width and a divergence of ions within the ion beam.

35. The analyzer of claim 34, wherein the spatially-focusing lens shares electrodes with or is incorporated into at least one of the ion source and the acceleration stage.

36. The analyzer of claim 32, further comprising a suppressor arranged as a field-fee region upstream of the buncher, said suppressor including at least one electrode connected to a pulse generator, wherein said pulse generator applies a pulsed voltage to the suppressor.

37. The analyzer of claim 36, wherein said at least one electrode of the suppressor is arranged to steer approaching ions, and wherein a single pulse generator applies the pulsed voltage to the suppressor and the pulsed voltage to one of a pair of parallel electrodes forming the buncher.

38. The analyzer of claim 36, wherein the suppressor comprises a bipolar mesh to push and deflect ions.

39. The analyzer of claim 32, wherein the time-of-flight mass separator comprises a singly reflecting time-of-flight mass spectrometer or a multi-reflecting time-of-flight mass spectrometer.

40. The analyzer of claim 32, wherein the buncher comprises:
two parallel electrodes; and
a pulsed generator providing a pulsed voltage to one of the two parallel electrodes (46).

41. The analyzer of claim 32, wherein the buncher comprises grid-free electrodes forming an electrostatic field.

42. The analyzer of claim 32, wherein the energy filter forms an isochronous curved inlet to the time-of-flight mass separator.

43. The analyzer of claim 32, wherein the energy filter comprises:
a planar lens arranged to spatially focus ion packets in a horizontal direction;
a first electrostatic sector;
a second electrostatic sector;
a third electrostatic sector;
a set of surrounding slits, one slit of the set located at an entrance and at an exit of each electrostatic sector; and
an energy filtering slit providing energy-level-based removal of outlier ions.

44. The analyzer of claim 32, wherein the energy filter comprises:
a separating slit; and
at least one of: angled ion mirrors, an electrostatic sector, deflectors, and one or more lenses.

45. The analyzer of claim 32, further comprising:
a gaseous radio frequency ion guide arranged to provide collisional dampening of an incoming ion beam;
an axial DC field;
a shield electrode; and
an extraction electrode,
wherein a combination of the shield electrode and the extraction electrode provide a field of spatial ion focusing.

46. The analyzer of claim 32, wherein the ion source comprises a closed EI ion source having an ion chamber; a repeller connected to a pulse generator; and an extractor connected to a pulse generator, wherein a gas chromatograph provides a sample to be analyzed be the analyzer.

47. The analyzer of claim 32, wherein the ion source comprises:
an accumulating ion guide formed by multipole rods;
an auxiliary push electrode receiving periodic soft extraction pulses;
an auxiliary DC trap electrode; and
an exit skimmer receiving periodic soft extraction pulses.

48. The analyzer of claim 46, further comprising a differential pumped tube, wherein the energy filter forms an isochronous curved inlet to the time-of-flight mass separator, and wherein the differential pumped tube receives ion packets from the buncher (47, 95, 108, 124) and passes the ion packets into the isochronous curved inlet.

49. The analyzer of claim 32, wherein the time-of-flight detector comprises:
a conductive converter receiving ion packets from a drift space of the time-of-flight mass separator;
at least one magnet forming a magnetic field deflecting electrons reflected by the conductive converter;

a positively-biased scintillator having a conductive mesh coating or covering and accepting electrons deflected by the magnetic field; and a sealed photomultiplier downstream from the positively-biased scintillator, wherein the conductive converter has a potential having a negative charge differing from the negative charge of a potential of the drift space.

50. The analyzer of claim 32 further comprising:

a time ion selector accessing parent ions separated in the time-of-flight separator;

a fragmentation cell accepting the parent ions from the time ion selector;

a fragmented ion mass analyzer accepting fragmented ions from the fragmentation cell; and a pulse generator connected to the time ion selector, wherein both the time-of-flight separator and the fragmented ion mass analyzer comprise either a singly reflecting time-of-flight mass spectrometer or a multi-reflecting time-of-flight mass spectrometer.

* * * * *